(12) United States Patent
Mudrik et al.

(10) Patent No.: US 9,476,811 B2
(45) Date of Patent: Oct. 25, 2016

(54) DIGITAL MICROFLUIDIC DEVICES AND METHODS INCORPORATING A SOLID PHASE

(75) Inventors: Jared M. Mudrik, Thornhill (CA); Hao Yang, Vancouver (CA); Aaron R. Wheeler, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 746 days.

(21) Appl. No.: 13/876,813

(22) PCT Filed: Oct. 3, 2011

(86) PCT No.: PCT/CA2011/050623
§ 371 (c)(1),
(2), (4) Date: Jul. 1, 2013

(87) PCT Pub. No.: WO2012/040861
PCT Pub. Date: Apr. 5, 2012

(65) Prior Publication Data
US 2013/0277218 A1    Oct. 24, 2013

Related U.S. Application Data

(60) Provisional application No. 61/388,942, filed on Oct. 1, 2010.

(51) Int. Cl.
*G01N 27/453* (2006.01)
*G01N 1/34* (2006.01)
(Continued)

(52) U.S. Cl.
CPC ........... *G01N 1/34* (2013.01); *B01L 3/502792* (2013.01); *B81B 1/00* (2013.01);
(Continued)

(58) Field of Classification Search
CPC ................... B01L 3/502792; B01L 3/502784; B01L 2400/0427
See application file for complete search history.

(56) References Cited

U.S. PATENT DOCUMENTS

| 4,569,575 A | 2/1986 | Le Pesant et al. |
| 4,636,785 A | 1/1987 | Le Pesant |

(Continued)

FOREIGN PATENT DOCUMENTS

| CA | 2740113 | 4/2010 |
| JP | 2010180222 A | 8/2010 |

(Continued)

OTHER PUBLICATIONS

Lee et al., "Removal of bovine serum albumin using solid-phase extraction with in-situ polymerized stationary phase in a microfluidic device," Journal of Chromatography A, 1187 (2008) 11-17.*

(Continued)

*Primary Examiner* — Alexander Noguerola
(74) *Attorney, Agent, or Firm* — Shay Glenn LLP

(57) ABSTRACT

Devices and methods are provided for performing droplet-based solid phase processing steps on a digital microfluidic device. A solid phase material, which may be a porous solid phase material such as a porous polymer monolith is formed or located on a digital microfluidic element. The solid phase may be formed by an in-situ method in which the digital microfluidic array is actuated to transport a droplet of solid phase pre-cursor solution to a selected element on the array, and subsequently processed to form a solid phase on the array element. The integration of a solid phase material with a digital microfluidic array enables a wide range of applications including solid phase extraction and sample concentration.

27 Claims, 11 Drawing Sheets

(51) Int. Cl.
  *C12N 15/10* (2006.01)
  *B81B 1/00* (2006.01)
  *B01L 3/00* (2006.01)

(52) U.S. Cl.
  CPC ..... *C12N 15/1003* (2013.01); *C12N 15/1006* (2013.01); *B01L 3/502753* (2013.01); *B01L 2200/0631* (2013.01); *B01L 2300/0636* (2013.01); *B01L 2300/089* (2013.01); *B01L 2300/0816* (2013.01); *B01L 2400/0427* (2013.01)

(56) References Cited

U.S. PATENT DOCUMENTS

| | | | |
|---|---|---|---|
| 4,818,052 | A | 4/1989 | Le Pesant et al. |
| 5,486,337 | A | 1/1996 | Ohkawa |
| 6,352,838 | B1 | 3/2002 | Krulevitch et al. |
| 6,565,727 | B1 | 5/2003 | Shenderov |
| 6,773,566 | B2 | 8/2004 | Shenderov |
| 6,887,384 | B1 | 5/2005 | Frechet et al. |
| 6,911,132 | B2 | 6/2005 | Pamula et al. |
| 6,989,234 | B2 | 1/2006 | Kolar et al. |
| 7,147,763 | B2 | 12/2006 | Elrod et al. |
| 7,163,612 | B2 | 1/2007 | Sterling et al. |
| 7,214,302 | B1 | 5/2007 | Reihs et al. |
| 7,255,780 | B2 | 8/2007 | Shendervo |
| 7,328,979 | B2 | 2/2008 | Decre et al. |
| 7,329,545 | B2 | 2/2008 | Pamula et al. |
| 7,445,926 | B2 | 11/2008 | Mathies et al. |
| 7,531,120 | B2 | 5/2009 | Van Rijn et al. |
| 7,713,456 | B2 | 5/2010 | Dodd et al. |
| 7,745,207 | B2 | 6/2010 | Jovanovich et al. |
| 8,053,239 | B2 | 11/2011 | Wheeler et al. |
| 8,202,736 | B2 | 6/2012 | Mousa et al. |
| 8,367,370 | B2 | 2/2013 | Wheeler et al. |
| 8,852,952 | B2 * | 10/2014 | Pollack ............ B01L 3/502715 436/174 |
| 2002/0150683 | A1 | 10/2002 | Troian et al. |
| 2003/0136451 | A1 * | 7/2003 | Beebe ............... B01L 3/502707 137/828 |
| 2004/0058450 | A1 * | 3/2004 | Pamula .............. B01F 13/0071 436/150 |
| 2004/0171169 | A1 | 9/2004 | Kallury et al. |
| 2004/0211659 | A1 | 10/2004 | Velev |
| 2005/0115836 | A1 | 6/2005 | Reihs |
| 2005/0148091 | A1 | 7/2005 | Kitaguchi et al. |
| 2005/0191759 | A1 | 9/2005 | Pedersen-Bjergaard et al. |
| 2007/0023292 | A1 | 2/2007 | Kim et al. |
| 2007/0095407 | A1 | 5/2007 | Chen et al. |
| 2007/0148763 | A1 | 6/2007 | Huh et al. |
| 2007/0242111 | A1 | 10/2007 | Pamula et al. |
| 2007/0243634 | A1 * | 10/2007 | Pamula .............. B01F 13/0071 436/518 |
| 2008/0044914 | A1 | 2/2008 | Pamula et al. |
| 2008/0110753 | A1 * | 5/2008 | Fourrier ............ B01L 3/502707 204/403.01 |
| 2008/0156983 | A1 | 7/2008 | Fourrier et al. |
| 2008/0185339 | A1 | 8/2008 | Delapierre et al. |
| 2008/0281471 | A1 | 11/2008 | Smith |
| 2009/0203063 | A1 | 8/2009 | Wheeler et al. |
| 2010/0081578 | A1 | 4/2010 | Wheeler et al. |
| 2010/0087633 | A1 | 4/2010 | Wheeler et al. |
| 2010/0213074 | A1 | 8/2010 | Mousa et al. |
| 2010/0311599 | A1 | 12/2010 | Wheeler et al. |
| 2011/0240471 | A1 | 10/2011 | Wheeler |
| 2012/0083046 | A1 | 4/2012 | Watson et al. |
| 2012/0085645 | A1 | 4/2012 | Mousa et al. |
| 2013/0164856 | A1 | 6/2013 | Jebrail et al. |

FOREIGN PATENT DOCUMENTS

| | | | |
|---|---|---|---|
| WO | WO-2004074169 A1 * | 9/2004 | ............ B81B 1/00 |
| WO | 2007120241 | 10/2007 | |
| WO | 2007130294 A2 | 11/2007 | |
| WO | 2007136386 | 11/2007 | |
| WO | 2008051310 | 5/2008 | |
| WO | 2008066828 A2 | 6/2008 | |
| WO | 2010040227 | 4/2010 | |
| WO | 2010111265 A1 | 9/2010 | |

OTHER PUBLICATIONS

Svoboda et al. "Cation exchange membrane integrated into a microfluidic device," Microelectronic Engineering vol. 86, issues 408, Apr.-Jun. 2009, pp. 1371-1374.*

Product description article entitled "Heterogeneous Ion-Exchange membranes Ralex®", downloaded from http://www.mega.cz/heterogenous-ion-exchange-membranes-ralex.html on Mar. 1, 2016.*

Kutter, J. P.; Jacobson, S. C.; Matsubara, N.; Ramsey, J. M. "Solvent-Programmed Microchip Open-Channel Electrochromatography", Analytical Chemistry 1998, 70, 3291-3297.

Kutter, J. P.; Jacobson, S. C.; Ramsey, J. M. "Solid phase extraction on microfluidic devices", Journal of Microcolumn Separations 2000, 12, 93-97.

Bergkvist, J.; Ekstrom, S.; Wallman, L.; Lofgren, M.; Marko-Varga, G.; Nilsson, J.; Laurell, T. "Improved chip design for integrated solid-phase microextraction in on-line proteomic sample preparation", Proteomics 2002, 2, 422-429.

Ekstrom, S.; Malmstrom, J.; Wallman, L.; Lofgren, M.; Nilsson, J.; Laurell, T.; Marko-Varga, G. "On-chip microextraction for proteomic sample preparation of in-gel digests", Proteomics 2002, 2, 413-421.

Ekstrom, S.; Wallman, L.; Hok, D.; Marko-Varga, G.; Laurell, T. "Miniaturized solid-phase extraction and sample preparation for MALDI MS using a microfabricated integrated selective enrichment target", Journal of Proteome Research 2006, 5, 1071-1081.

Ekstrom, S.; Wallman, L.; Helldin, G.; Nilsson, J.; Marko-Varga, G.; Laurell, T. "Polymeric integrated selective enrichment target (ISET) for solid-phase-based sample preparation in MALDI-TOF MS", Journal of Mass Spectrometry 2007, 42, 1445-1452.

Jemere, A. B.; Oleschuk, R. D.; Ouchen, F.; Fajuyigbe, F.; Harrison, D. J. "An integrated solid-phase extraction system for sub-picomolar detection", Electrophoresis 2002, 23, 3537-3544.

Li, J.; LeRiche, T.; Tremblay, T. L.; Wang, C.; Bonneil, E; Harrison, D. J.; Thibault, P. "Application of microfluidic devices to proteomics research: identification of trace-level protein digests and affinity capture of target peptides", Molecular & cellular proteomics : MCP 2002, 1, 157-168.

Oleschuk, R. D.; Shultz-Lockyear, L. L.; Ning, Y.; Harrison, D. J. "Trapping of bead-based reagents within microfluidic systems: On-chip solid-phase extraction and electrochromatography", Analytical Chemistry 2000, 72, 585-590.

Lettieri, G. L.; Dodge, A.; Boer, G.; De Rooij, N. F.; Verpoorte, E. "A novel microfluidic concept for bioanalysis using freely moving beads trapped in recirculating flows", Lab on a Chip—Miniaturisation for Chemistry and Biology 2003, 3, 34-39.

Foote, R. S.; Khandurina, J.; Jacobson, S. C.; Ramsey, J. M. "Preconcentration of proteins on microfluidic devices using porous silica membranes", Analytical Chemistry 2005, 77, 57-63.

Hatch, A. V.; Herr, A. E.; Throckmorton, D. J.; Brennan, J. S.; Singh, A. K. "Integrated preconcentration SDS-PAGE of proteins in microchips using photopatterned cross-linked polyacrylamide gels", Analytical Chemistry 2006, 78, 4976-4984.

Petersen, N. J.; Jensen, H.; Hansen, S. H.; Foss, S. T.; Snakenborg, D.; Pedersen-Bjergaard, S. "On-chip electro membrane extraction", Microfluidics and Nanofluidics 2010, 1-8.

Bonneil, E.; Li, J.; Tremblay, T. L.; Bergeron, J. J.; Thibault, P. "Integration of solid-phase extraction membranes for sample multiplexing: Application to rapid protein identification from gel-isolated protein extracts", Electrophoresis 2002, 23, 3589-3598.

Yu, C.; Davey, M. H.; Svec, F.; Frechet, J. M. J. "Monolithic porous polymer for on-chip solid-phase extraction and preconcentration prepared by photoinitiated in situ polymerization within a microfluidic device", Analytical Chemistry 2001, 73, 5088-5096.

(56) References Cited

OTHER PUBLICATIONS

Yu, C.; Xu, M.; Svec, F.; Frechet, J. M. J. "Preparation of monolithic polymers with controlled porous properties for microfluidic chip applications using photoinitiated free-radical polymerization", Journal of Polymer Science, Part A: Polymer Chemistry 2002, 40, 755-769.
Lee, J.; Moon, H.; Fowler, J.; Schoellhammer, T.; Kim, C. J. "Electrowetting and electrowetting-on-dielectric for microscale liquid handling", Sensors and Actuators, A: Physical 2002, 95, 259-268.
Pollack, M. G.; Fair, R. B.; Shenderov, A. D. "Electrowetting-based actuation of liquid droplets for microfluidic applications", Applied Physics Letters 2000, 77, 1725-1726.
Wheeler, A. R. "Chemistry: Putting electrowetting to work", Science 2008, 322, 539-540.
Abdelgawad, M.; Freire, S. L. S.; Yang, H.; Wheeler, A. R. "All-terrain droplet actuation", Lab on a Chip—Miniaturisation for Chemistry and Biology 2008, 8, 672-677.
Jebrail, M. J.; Wheeler, A. R. "Digital microfluidic method for protein extraction by precipitation", Analytical Chemistry 2009, 81, 330-335.
Mousa, N. A. J., M.J.; Yang, H.; Abdegawad, M.; Metalnikov, P.; Chen, J.; Wheeler, A.R.; Casper, R.F. "Droplet-Scale Estrogen Assays in Breast Tissue, Blood, and Serum", Sci. Trans. Med. 2009, 1, 1ra2.
Jebrail, M.J.; Luk, V. N.; Shih, S.C.C.; Fobel, R.; Ng, A.H.C.; Yang, H.; Freire, S.L.S.; Wheeler, A.R. Journal of Visualized Experiments. 2009, 33, DOI: 10.3791/1603.
Millington, D.S., et al., Digital Microfluidics: A Novel Platform for Multiplexed Detection of LSDs with Potential for Newborn Screening, Oak Ridge Conference (2009).
Millington, D.S., et al., Digital Microfluidics: A Future Technology in the Newborn Screening Laboratory?, Sem. In Perinat. 34 (2), 163-169 (2010).
Shih-Kang Fan. Cross-scale electric manipulations of cells and droplets by frequency-modulated dielectrophoresis and electrowetting. The Royal Society of Chemistry (2008), Lab Chip vol. 8, pp. 1325-1331.
Ting-Hsuan Chen. Selective Wettability Assisted Nanoliter Sample Generation Via Electrowetting-Based Transportation. Proceedings of the Fifth International Conference on Nanochannels, Microchannels and Minichannels (ICNMM) (Jun. 18-20, 2007).

Hongmei Yu. A plate reader-compatible microchannel array for cell biology assays. The Royal Society of Chemistry (2007) Lab Chip vol. 7, pp. 388-391.
Marc A. Unger. Monolithic Microfabricated Valves and Pumps by Multilayer Soft Lithography. Science (2000) vol. 288.
A.S. Verkman. Drug Discovery in Academia. Am J Physiol Cell Physiol (2004) vol. 286, pp. 465-474.
Jamil El-Ali. Cells on chips. Nature (2006) Insight Review. vol. 442.
Darren R. Link. Electric Control of Droplets in Microfluidic Devices. Communications. Angew Chem. Int (2006) vol. 45 pp. 2556-2560.
Wheeler Aaron A. Electrowetting-Based Microfluidics for Analysis of Peptides and Proteins by Matrix-Assisted Laser Desorption/Ionization Mass Spectrometry. (Aug. 2004) Anal Chem. vol. 76, No. 16.
Eun Zoo Lee. Removal of bovine serum albumin using solid-phase extraction with in-situ polymerized stationary phase in a microfluidic device. ScienceDirect. Journal of Chromatography A. (2008) vol. 1187. pp. 11-17.
Hsih Yin Tan. A lab-on-a-chip for detection of nerve agent sarin in blood. The Royal Society of Chemistry (2008). Lab Chip vol. 8. pp. 885-891.
Kai-Cheng Chuang. Direct Handwriting Manipulation of Droplets by Self-Aligned Mirror-EWOD Across a Dielectric Sheet. MEMS (Jan. 2006) pp. 22-26.
Mohamed Abdelgawad. Low-cost, rapid-prototyping of digital microfluidics devices. Springer. Microfluid Nanofluid (2008) vol. 4. pp. 349-355.
Eric Lebrasseur. Two-dimensional electrostatic actuation of droplets using a single electrode panel and development of disposable plastic film card. ScienceDirect. Sensors and Actuators (2007) vol. 136. pp. 358-366.
Chatterjee et al. Droplet-based microfluidics with nonaqueous solvents and solutions. Lap Chip. 2006. vol. 6. pp. 199-206.
Jebrail et al. Digital Microfluidic Method for Protein Extraction by Precipitation. Analytical Chemistry. Jan. 1, 2009. vol. 81. No. 1. pp. 330-335.
Moon et al., "An integrated digital microfluidic chip for multiplexed proteomic sample preparation and analysis by MALDI-MS", Lab Chip, 2006, vol. 6, pp. 1213-1219.

\* cited by examiner (a)

(b)

DIGITAL MICROFLUIDIC DEVICES AND METHODS INCORPORATING A SOLID PHASE

CROSS-REFERENCE TO RELATED APPLICATION

This application is a National Phase application claiming the benefit of No. PCT/CA2011/050623 filed on Oct. 3, 2011, in English, which further claims priority to U.S. Provisional Application No. 61/388,942, titled "DIGITAL MICROFLUIDIC DEVICES AND METHODS INCORPORATING A SOLID PHASE" and filed on Oct. 1, 2010, the entire contents of which are incorporated herein by reference.

BACKGROUND

This disclosure relates to microfluidic devices for sample preparation, processing, purification, and extraction with a solid phase.

Most samples that are collected for diagnostic testing are complex mixtures of analytes and matrix. In many cases, the matrix includes many undesirable constituents that can interfere with analysis. Complicating matters further, analytes are often present at very low concentrations relative to the highly abundant matrix constituents. Thus, a critical step in many applications is sample preparation, isolation and extraction.

In many assay protocols, the analyte must first be separated from the matrix and often concentrated prior to analysis. The most common method for sample preparation is solid phase extraction (SPE), which exploits interactions between a liquid sample and a solid stationary phase material (often formed from a packed bed of beads or a porous polymer monolith). When a liquid sample is passed over or through the stationary phase, analyte is retained on the solid phase while matrix compounds are washed away. Traditionally, the stationary phase is hydrophobic (similar to reversed-phase media for chromatography), which facilitates purification of non-polar analytes from polar constituents. After washing the solid phase, analyte retained within the solid phase may be eluted in a different solvent (which has high affinity for the analytes), which may have a volume that is smaller than the initial sample volume, thereby concentrating the extracted analyte. The purified sample is then ready for analysis.

Although SPE is ubiquitous for sample preparation using macroscale protocols and systems, SPE has recently been applied to microchannels to take advantage of the high surface-to-volume ratios and short diffusion distances exhibited within microchannels. The microchannel-based SPE techniques reported previously have employed solid-phase materials formed directly on channel walls,[1,2] from packed beds of beads,[3-10] from porous membranes,[11-14] and from porous polymer monoliths (PPM).[15,16]

Despite these developments, the microchannel-based SPE methods reported previously are not useful for some applications. For example, such methods are typically not amenable to preparative-scale applications, because samples handled in microchannels may be difficult to recover.

SUMMARY

Devices and methods are provided for performing droplet-based solid phase processing steps on a digital microfluidic device. A solid phase material, which may be a porous material such as a porous polymer monolith, is formed or located on a digital microfluidic element. The solid phase may be formed by an in-situ method in which the digital microfluidic array is actuated to transport a droplet of solid phase pre-cursor solution to a selected element on the array, and subsequently processed to form a solid phase on the array element. The integration of a solid phase material with a digital microfluidic array enables a wide range of applications including solid phase extraction and sample concentration.

Accordingly, in a first aspect, there is provided a digital microfluidic device including a substrate; an array of electrically addressable digital microfluidic elements provided on the substrate; and a solid phase material contacting an element of the array; wherein the solid phase material is positioned such that a liquid droplet is contacted with the solid phase material when the liquid droplet transported to the element.

In another aspect, there is provided a digital microfluidic device including a substrate; an array of electrically addressable digital microfluidic elements provided on the substrate; and a solid phase material provided on an element of the array.

In another aspect, there is provided a method for performing solid phase extraction of a species from a sample, the method including the steps of providing a digital microfluidic device including a substrate, an array of electrically addressable digital microfluidic elements provided on the substrate, and a solid phase material contacting an element of the array; providing a liquid sample at a location addressable by the array; actuating the array to transport a sample droplet to contact the element such that the sample droplet contacts the solid phase material; incubating the sample droplet while maintaining contact of the sample droplet with the solid phase material; transporting the sample droplet to another location addressable by the array; providing an elution buffer at a location addressable by the array, wherein elution buffer is suitable for eluting the species from the solid phase material; actuating the array to transport an elution buffer droplet to the element; and incubating the elution buffer droplet while maintaining contact of the elution buffer droplet with the solid phase material for a time suitable for elution of the species from the solid phase material to the elution buffer droplet.

In another aspect, there is provided a method of forming a solid phase in-situ on a digital microfluidic device, the method including the steps of: providing first plate including a substrate having formed thereon an array of electrically addressable digital microfluidic elements, wherein each element of the array includes an electrode coated with an electrical insulating layer having a hydrophobic surface; providing a solid phase precursor solution at a location addressable by the array; providing a second plate including an electrode coated with a layer having a hydrophobic surface, and forming a two-plate digital microfluidic device by providing a spacer for defining a gap between the first plate and the second plate; actuating the electrodes to transport a precursor droplet to contact an element of the array; and processing the precursor droplet to form the solid phase on the element.

In another aspect, there is provided a method of forming a solid phase on a selected element of a digital microfluidic device including the steps of actuating the device to transport a precursor droplet of a solid phase precursor solution to the selected element, and processing the precursor droplet to form the solid phase on the selected element.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "solid phase" refers to non-liquid solid and stationary phase materials.

As used herein, the term "species", as employed with regard to a sample containing a species, shall refer to elemental species, ionic species, molecular species, biomolecular species, complexed species, and other species which is or are suitable for separation and/or extraction according to the present disclosure. A species may be an analyte to be assayed or otherwise determined.

In contrast to known methods of solid phase extraction (SPE) involving microfluidic channels, embodiments of the disclosure as described below provide devices and methods that incorporate a solid phase material within a digital microfluidic (DMF) device. DMF-based droplet transport operations according to embodiments provided below employ one or more DMF array elements that include an intra-element solid phase material for on-chip separation. Additional embodiments provide methods for forming, in-situ, a solid phase material on a DMF array element, thus providing a solid phase array element within the array. The solid phase is may be a porous material.

Figure 1:
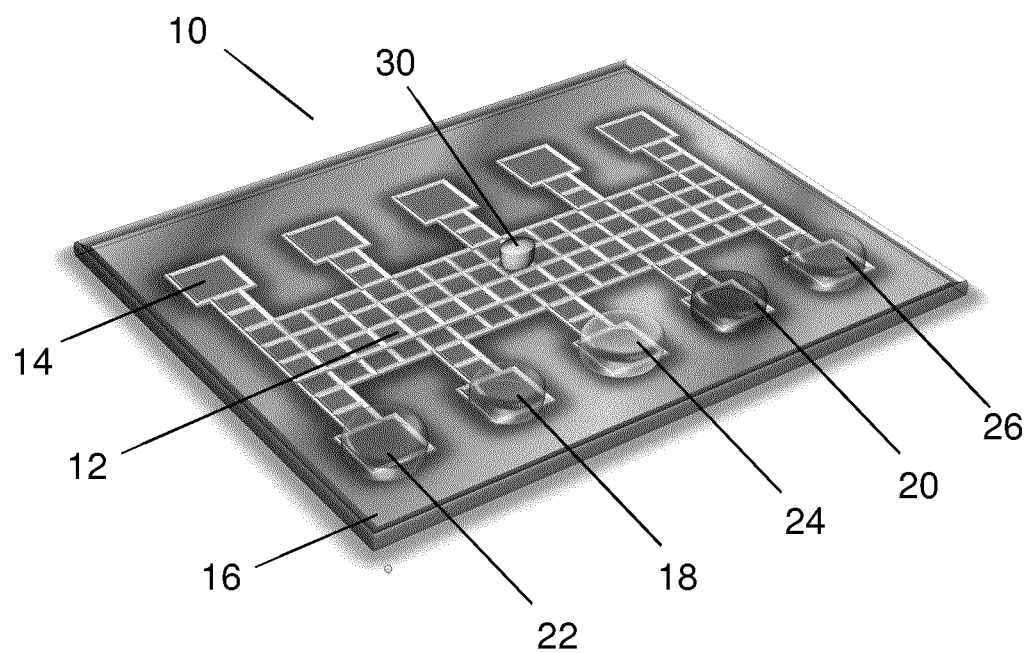
FIG. 1 is an illustration showing a digital microfluidic (DMF) device incorporating a solid phase extraction (SPE) material.

Referring to FIG. 1, an example DMF device 10 is shown including an array of small DMF array elements 12 (for droplet transport within the array), larger array elements 14 (which may be utilized, for example, as reagent reservoirs, or, for example, as waste or collector reservoirs), and substrate 16. Device 10 also includes contact pads (not shown) connected to each electrode for external actuation. The array elements 12 and 14 each include electrodes formed on a substrate, where each electrode is coated with a dielectric layer having a hydrophobic surface, and the hydrophobic surface may be provided as an additional layer formed on the dielectric layer. In one example implementation, electrodes 12 and 14 may be formed in part or in whole from chromium, and the insulating layer may be a layer of an electrically insulating polymer such as parylene, which may be further coated with a hydrophobic layer such as Teflon®. Droplet transport on the array is achieved by the application of a potential between adjacent electrodes within the array.

FIG. 1 illustrates several different liquids initially residing at large reservoir electrodes. Such liquids may include a sample 18, a wash buffer 20, an elution buffer 22, and may further include a monomer solution 24, and an activation solution 26 for the in-situ fabrication of a solid phase 30 on an array element, as further described below.

As noted above, one or more of large electrodes 14 may be employed as waste reservoirs. Although electrodes 14 are shown as being larger than intra-array electrodes 12, it is to be understood that this is merely one example implementation, and that other embodiments may be employed in which electrodes 12 and 14 have different relative sizes. In other examples, the DMF array may not include reservoir array elements, and liquids may instead be directly transferred onto array elements 12, for example, using a pipettor or other liquid dispensing device.

The DMF device may be provided as a one-plate array, or a two-plate array. The device shown in FIG. 1 is the bottom plate of two-plate array, and the two-plate device further includes a top plate and an electrically insulating spacer defining a gap between the two plates where droplet transport may occur. The top plate provides at least one upper electrode (which may be coated with a hydrophobic and insulating layer), and droplet actuation is achieved by applying potential difference between the upper electrode(s) and the electrodes on the bottom plate. The top plate may be transparent to enable imaging or other forms of optical detection or monitoring during device actuation. The top plate may be removable to facilitate the dispensing of liquids onto DMF array elements prior to device operation.

Figure 2:
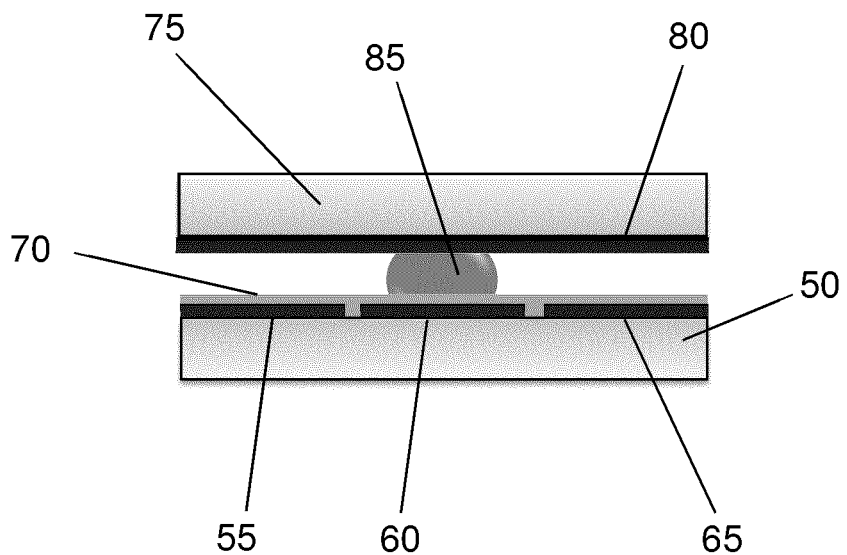
FIG. 2 is an illustration of a two-plate DMF device having an integrated solid phase.

FIG. 2 shows a side view illustrating both plates of a two-plate DMF device having an integrated solid phase 85 located at an array element 60. The device includes bottom plate 50, which has formed thereon electrodes 55, 60 and 65, with insulating and hydrophobic coating 70, and top plate 75, having top contact and hydrophobic layer 80 (an optional dielectric layer for top plate 75 is not shown. Formed between both plates is solid phase 85, which, in one embodiment, may be a porous polymer monolith, as further described below.

The inclusion of a top plate to form a two-plate device provides a convenient device for the in-situ fabrication of a solid phase on an array element using digital microfluidic droplet transport and processing. In one embodiment, a solid phase may be formed on a DMF array element according to the following method. For purposes of teaching only, the solid phase material described in the forthcoming example and non-limiting method is a porous polymer monolith (PPMs). However, it is to be understood that the method is not limited to PPM-based solid phase materials, and may be adapted to any method of forming a solid phase that is compatible with droplet transport and processing.

The method is illustrated with reference to the flowchart provided in FIG. 3. In step 100, one or more solid phase precursor solutions for forming the solid phase are dispensed onto array elements, for example, at reservoir array elements 14.

For example, in the case of a solid phase formed from a PPM, a single precursor or casting solution may be prepared as follows. A C12 casting solution may be prepared by mixing butyl acrylate, 1,3-butanediol diacrylate, lauryl acrylate, 2,2-dimethoxy-2-phenylacetophenone, and porogen. Example quantities of these components include 279 µL of butyl acrylate, 150 µL of 1,3-butanediol diacrylate, 69 µL of lauryl acrylate, 2.5 mg of 2,2-dimethoxy-2-phenylacetophenone, and 1 mL of porogen, where the porogen may include a 4:1:1 ratio of acetonitrile, 95% ethanol, and 5 mM phosphate buffer at pH 6.8.

Similarly, a C18 casting solution may be prepared by mixing 2,2-dimethoxy-2-phenylacetophenone, butyl acrylate, octadecyl acrylate, 1,3-butanediol diacrylate, and a porogen. Example quantities of these components include 2.5 mg of 2,2-dimethoxy-2-phenylacetophenone, 276 µL of butyl acrylate, 275 µL of octadecyl acrylate (0.3 g/mL in tetrahydrofuran), 150 µL of 1,3-butanediol diacrylate, and 796 µL of porogen, which may include a 3:1:1 ratio of acetonitrile, 95% ethanol, and 5 mM phosphate buffer at pH 6.8.

In another example, a casting solution for the formation of strong cation exchange (SCX) monoliths may be prepared by dissolving glycidyl methacrylate, ethylene glycol dimethacrylate and 2,2-dimethoxy-2-phenylacetophenone in a porogenic solvent. Example quantities of these components include 900 µL of glycidyl methacrylate, 300 µL of ethylene glycol dimethacrylate and 12 mg of 2,2-dimethoxy-2-phenylacetophenone in a porogenic solvent consisting of 1.05 mL of 1-propanol, 600 µL of 1,4-butanediol and 150 µL of water.

It is to be understood that the preceding quantities are provided as examples only and are not intended to limit the scope of the disclosure. Those skilled in the art will appreciate that the specific volumes of monomer solutions, porogen, buffers and other solutions may be varied from the aforementioned values for forming a PPM.

In the case of a single precursor solution, the single solution is dispensed onto the array element, and the array is actuated to transport one or more droplets of the precursor solution to a selected array element where the solid phase is to be formed, as shown in step 110. The actuation of the array is performed by applying voltages between the top plate electrode and the bottom plate electrode. In step 120, the droplet is processed to form the solid phase on the array element. The processing may include any suitable processing step compatible with a digital microfluidic platform, including, but not limited to, photo-polymerization, and thermal curing.

In the exemplary case of the formation of a PPM based on a precursor solution as described above, the formation of the PPM is may be initiated via photo-polymerization. This is readily achieved using a top plate that is transparent and includes a transparent conductive electrode such as indium tin oxide. In an alternative example, thermal curing may be performed by incubating the device within a suitable thermally controlled environment, such as an oven.

In step 130, a droplet of activation solvent may be transported to the solid phase for activation of the solid phase. Activation permits reproducible retention of analytes by ensuring the solid phase exists in a substantially identical environment at the beginning of each extraction. In the case of hydrophobic solid phases, activation also serves to enable the diffusion of aqueous samples into the hydrophobic phase. The activation step may be performed immediately prior to use. In the case of a PPM as described above, a suitable activation solvent is acetonitrile and formic acid. Finally, in step 140, after incubating the activation droplet for a suitable time period, the activation droplet is removed from the solid phase and transported from the array element to another location on the array (such as a waste reservoir).

While the above method has been described for forming a solid phase on an array element of a two-plate DMF device, a similar protocol can be achieved to form a solid phase on a one-plate DMF device. In a one embodiment, this may be achieved by providing a one-plate DMF device, and also providing a spacer and top plate that temporarily forms a two-plate device from the one-plate device. The aforementioned processing steps may then be performed to form a solid phase on an array element. After having formed to the solid phase, the top plate may be removed, thereby providing a one-plate DMF device with an integrated solid phase. An example of such a device is provided below in Example 6.

It is to be understood that solid phase materials may be formed on a DMF device according to additional methods than the in-situ DMF processing steps described above. In one embodiment, the precursor solution(s) may be dispensed onto the desired array element by a dispensing device or method other than DMF droplet actuation, for example, by manually pipetting.

Although the inventors have found that the solid phase structures formed from porous polymer monoliths remain intact after having been formed on a non-stick (Teflon®) surface, the DMF device may be pre-processed to provide improved attachment of the solid phase to the DMF surface. In one embodiment, the surface of the DMF device may be locally masked while depositing the hydrophobic layer of the device, where the mask is provided on a portion of the array element on which a solid phase structure is to be formed. Subsequent removal of the local intra-element mask then provides improved surface adhesion properties for anchoring the solid phase, while maintaining hydrophobicity over another portion of the array element for supporting droplet transport. In one example implementation, the mask may be applied over only a central region of the array element.

In other embodiments, a solid phase may be formed externally and subsequently adhered to the DMF array via a processing step such as thermal processing and mechanical fixing via applied pressure from above. In one embodiment, a solid phase may be mechanically supported over an array element from a vertical or lateral location, thus enabling contact of the solid phase with droplets on the DMF array while not impeding droplet transport operations. Such an embodiment is also suitable to one-plate DMF devices. For example, a solid phase could be clamped or otherwise mechanically secured by a fixture, with the fixture positioned over the desired DMF array element. One or more lateral features may also be included to prevent or restrict motion of the solid phase during droplet actuation, where the lateral features are positioned such that droplet transport to and from the solid phase is not impeded.

In another embodiment, the surface of the DMF element on which the solid phase material is to be located may be modified to allow the solid phase material to be covalently bound to its surface. In one example implementation, the DMF element surface is modified (prior to placement or formation of a PPM phase) to include acrylate moieties, which become covalently bound to the PPM during on-chip UV photopolymerization.

In another embodiment, multiple solid phases with identical or different functionalities may be positioned over separate DMF elements on the same device. This enables multiple solid-phase extractions to be performed individually or in series on a single DMF device. The above methods may be performed to provide and form any solid phase material that is compatible with droplet-based transport and delivery. Non-limiting examples of such solid phase substances include strong cation exchange PPMs, strong anion exchange PPMs, weak cation exchange PPMs, weak anion exchange PPMs, normal phase PPMs, acrylamide gels, agarose gels, hydrogels, chiral PPMs, trapped glass beads, trapped polymeric beads, and affinity phases where a small molecule has an affinity for a large molecule. In one embodiment, beads, for example activated, conjugated or functionalized beads, may be trapped within a monolithic structure for forming a solid phase, as shown in Example 7 below.

In one embodiment, the size of the solid phase is selected to have a lateral cross section (within a plane parallel to the digital microfluidic array) that is less than that of the array element on which the solid phase resides. For example, as shown in FIG. 2, a solid phase formed according to a photo-polymerization process typically occupies a spatial region that forms a cylindrical segment near the central portion of an array element. By selecting the size of the solid phase to be less than that of the array element, droplet actuation onto and away from the array element is made more efficient, as a smaller volume of solid phase produces a smaller perturbation or disturbance to droplet transport. Accordingly, in some embodiments, the spatial profile of a photopolymerizing beam is selected and/or controlled to control the lateral size of the photopolymerized solid phase.

DMF based devices incorporating a solid phase according to embodiments disclosed herein provide new platforms and methods in which discrete droplets are manipulated on an array of electrodes by application of electromechanical forces. As noted above, past efforts to incorporate solid phase materials focused on microchannels, in which PPMs have been prepared in enclosed microchannels for on-chip SPE and preconcentration[1-16]. In microchannels, fluid flow through the monolith is commonly driven by electro-osmotic flow (EOF). Although the flat profile of EOF is useful for very efficient separations, EOF can only be achieved with a limited number of solvents and requires the use of low ionic strength buffer to avoid excessive joule heating within the microchannel. In addition, microchannel based SPE techniques are not suited for preparative-scale applications, as samples handled in microchannels are difficult to recover for further processing.

In contrast to the limitations of microchannel based SPE devices, DMF based solid phase devices are very well suited for preparative applications such as SPE, which involves sequentially exposing the stationary phase (PPM in this case) to solvents and phases. Moreover, DMF is compatible with organic solvents commonly used for conventional ZipTip® or cartridge-type SPE. This is clearly illustrated in FIG. 5 (as further described in the Examples below) in which it is shown that droplets ranging in composition from the aqueous wash buffer (0.5% v/v formic acid) to pure acetonitrile (activation solvent) may be transported on the array without any difficulty despite the presence of the stationary phase.

The ability to integrate SPE as a cleanup step using PPMs with other sample preparation steps on a single DMF device is particularly useful for enabling a fully integrated microanalytical system. The incorporation of DMF techniques combined with many other different polymeric monolith materials as stationary phases will permit the development of innovative, potentially automatable micro total analysis systems (μTAS) devices. Suitable stationary phases for incorporation with DMF array elements include, but are not limited to, PPM monoliths, hydrogels, beads with geometric constraints (such as, for example, entrapment or a physical wall or barrier surrounding the beads) and modified forms thereof comprising functionalized and/or bio-active compositions.

DMF devices with stationary phases according to various embodiments may be employed for a wide range of sample processing steps, including, but not limited to, hydrophobic interactions, ion exchange, and antibody-antigen interaction. Accordingly, embodiments incorporating a solid or stationary phase on or above a DMF array element may be useful in a wide range of sample processing applications that are not limited to solid phase extraction. An additional exemplary yet non-limiting application includes fractionation of a complex mixture using consecutive elution buffers of varying composition.

Figure 4A:
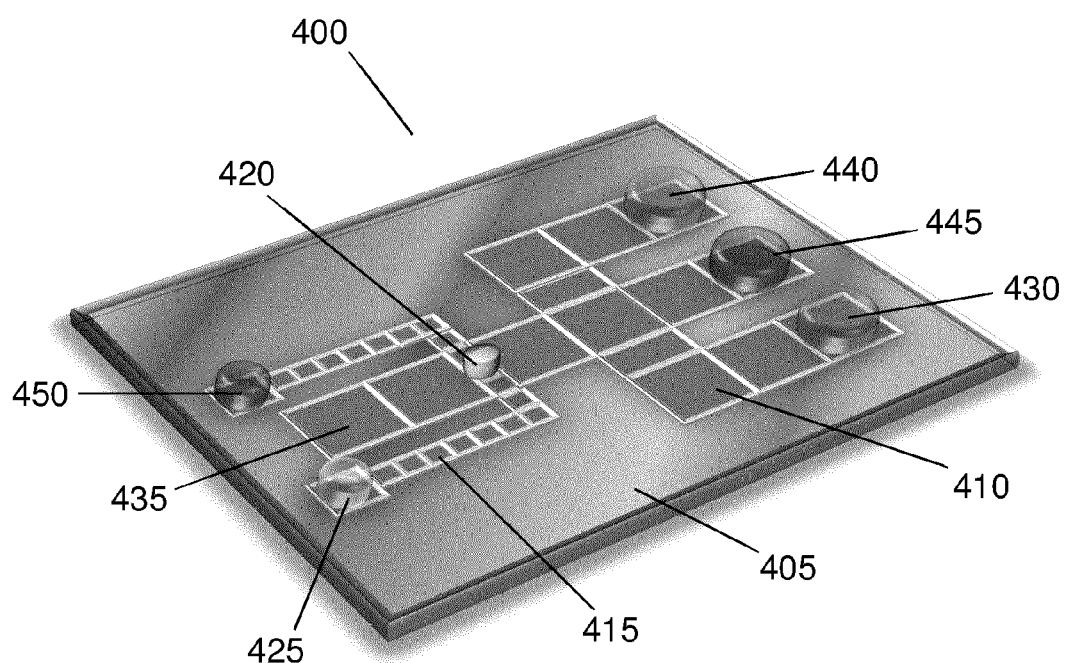
FIG. 4 is an illustration showing a DMF device design for preconcentration, including large electrodes for sample, activation, and washing solvents, and small electrodes for elution buffer and optional polymer casting solution for in-situ preparation of a solid phase extraction polymer monolith.

In another embodiment, a DMF device having a solid phase provided or formed on an array element may be employed for sample pre-concentration. An example implementation of a DMF SPE device 400 for achieving sample pre-concentration is illustrated in FIG. 4, which shows only the bottom plate 405 of a two-plate device. The device includes an array of large electrodes 410 that is intersected by an array of smaller electrodes 415. Although the specific configurations of the device may vary depending on the application, the device shown in FIG. 4 provides a non-limiting example in which a solid phase may be formed in-situ, and subsequently employed for a sample preconcentration step.

Figure 3:
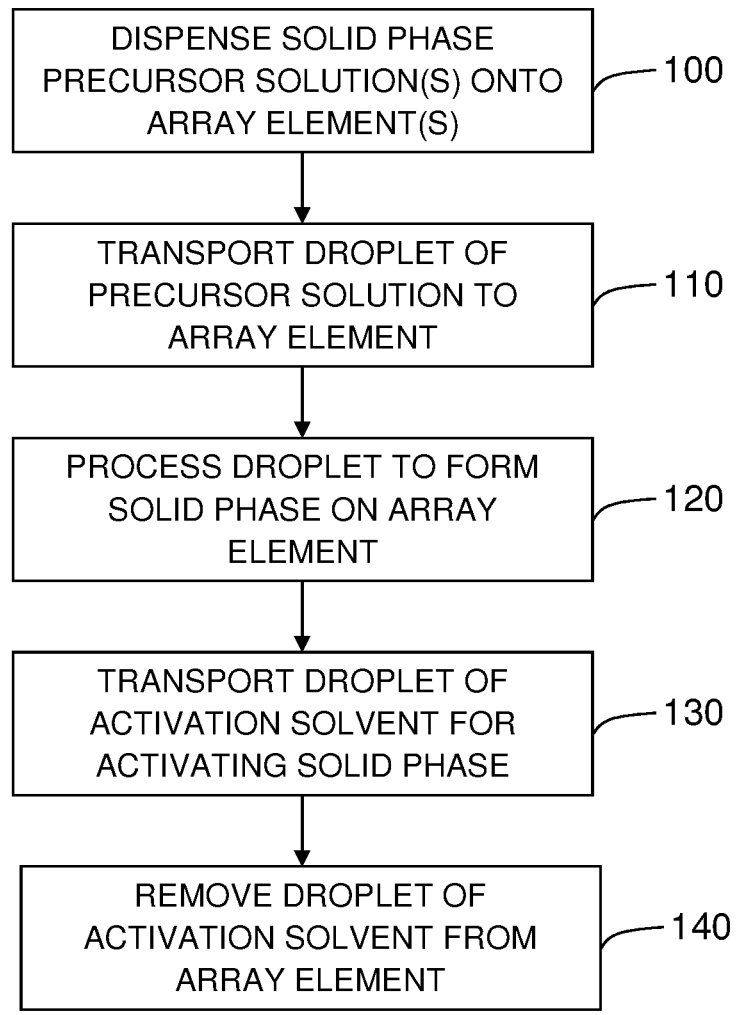
FIG. 3 is a flow chart describing a method of forming, in-situ, a solid phase on a DMF array element.

The solid phase 420 may be formed on a small electrode, at a location where the small electrode array intersects the large electrode array, according to a method similar to that illustrated in FIG. 3. A precursor solution for forming a solid phase initially resides at electrode 425 and a droplet is subsequently transported by actuation of the DMF array to a small electrode positioned at the intersection of the large electrode array and small electrode array. The droplet is processed to form the solid phase, for example, by photopolymerization.

The solid phase is then activated by a droplet of activation solvent, which is transported via actuation of the large array electrodes from an initial location 430 (the activation solution may alternatively be initially provided on the small electrode array and one or more droplets may be transported to the solid phase by actuation of the small electrodes). After incubation, the activation droplet is transported to a waste location, such as large electrode 435.

It is to be understood that the formation and activation of the solid phase is not intended to be limited to in-situ dispensing via DMF electrode actuation, and in other embodiments, the formation and/or activation of the solid phase may be performed by dispensing (manually or robotically) liquids using an off-chip dispensing device such as a pipettor or a pumping device (e.g. a syringe pump).

Figure 4B:
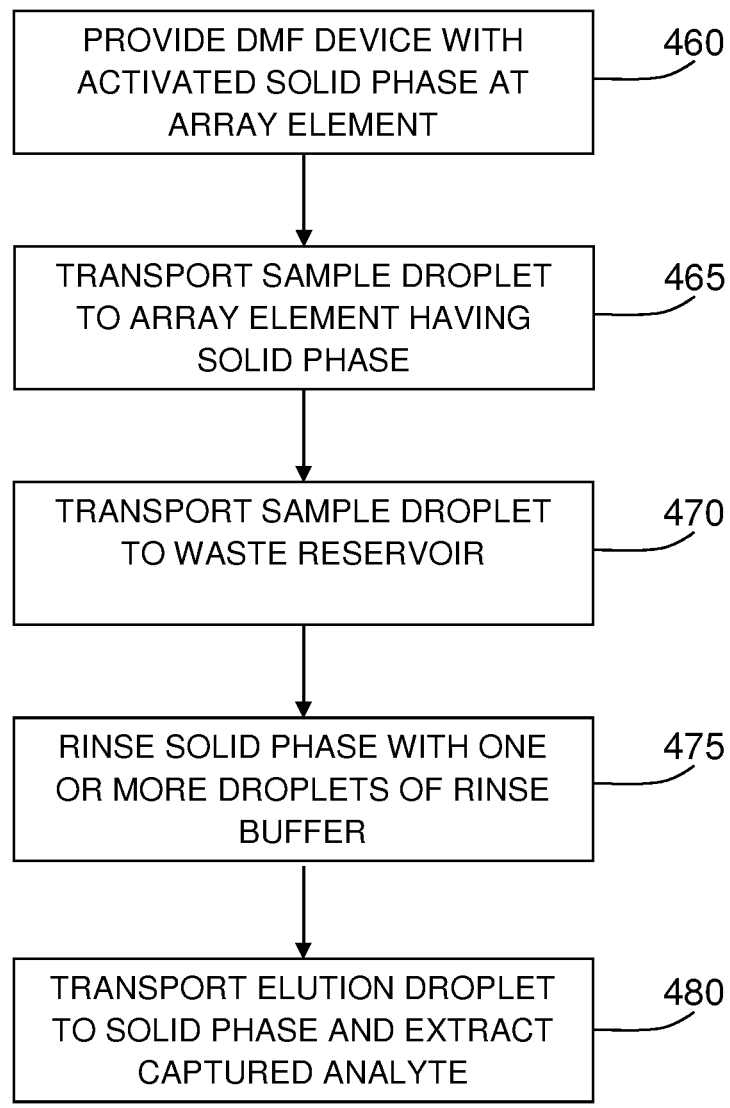

Having activated the solid phase, a species may be extracted from a sample droplet as follows. Referring now to FIG. 4(b), a DMF device with an activated solid phase at an element of the array (e.g. at 420 in FIG. 4(a)) is provided in step 460. A sample droplet is then transported from an initial electrode (e.g. large electrode 440) to the solid phase using the large array electrodes in step 465. After having completed the extraction step, the sample droplet may be transported to a waste electrode/reservoir in step 470, and the solid phase is rinsed or washed with one or more droplets of rinse/wash buffer in step 475 (e.g. that resides at large electrode 445 in FIG. 4(a)).

The extracted species may then be eluted using a droplet of elution buffer as shown in step 480, which is dispensed from initial location 450 and transported to the solid phase. The amount of preconcentration is determined by the electrode size differential (i.e. large electrodes for sample versus small electrodes for elution buffer). This is further evidenced in Example 3 below, in which fluorescein was preconcentrated by a factor of up to 9 times using a DMF SPE device.

In one embodiment, any steps related to sample processing using the solid phase that rely on diffusion may be improved by actuation of the electrode array to produce motion of a droplet relative to the solid phase. For example, during an extraction step, a sample droplet may be moved back and forth across the solid phase.

Figure 13:
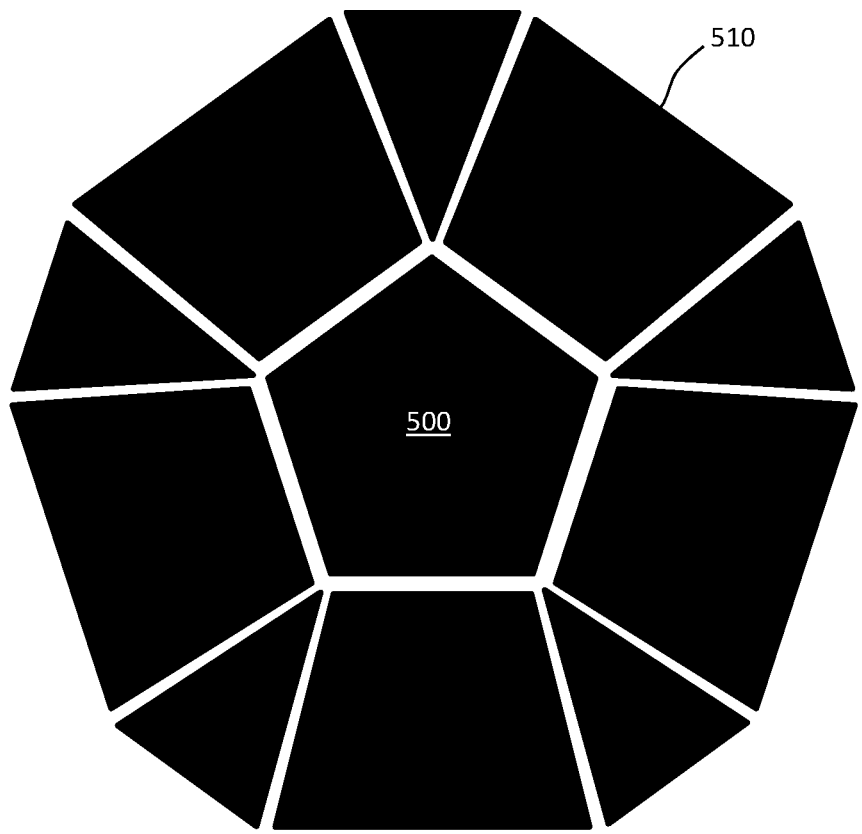
FIG. 13 provides an example arrangement of DMF elements for allowing vortex-like motion of a droplet around a central DMF element supporting a solid phase.

Alternatively, a spatial distribution of electrodes adjacent to the array element supporting the solid phase may be selected to allow more complex droplet motion, such as a motion that mimics orbital vortexing. FIG. 13 illustrates an example implementation of such an electrode arrangement, where a central electrode 500 (shown as having a pentagonal shape) is surrounded by electrodes 510 for actuating droplet motion relative to the central electrode.

It is noted that although preconcentration factors up to 1000 times have been demonstrated in microchannels by Yu et al.,[15] preconcentrated samples in such case were directed to a subsequent detection step without further processing. Unlike the DMF-SPE based preconcentration methods disclosed herein, such microchannel based preconcentration methods are not suitable for preparative-scale applications, as preconcentrated samples may require further modifications such as fluorescent labelling and digestion prior to detection.

As shown in Example 2 below, a direct comparison was made of the extraction efficiency of a C18 PPM formed on DMF array element to that of commercially available ZipTips®. The extraction efficiency of C18 PPMs was comparable to the performance of C18 ZipTips®, even though parameters such as sample loading time and number of elution droplets had been optimized for C12 PPMs (without intending to be limited by theory, the observed discrepancy is believed to be mainly due to inefficient mass transfer between the two phases).

Figure 7:
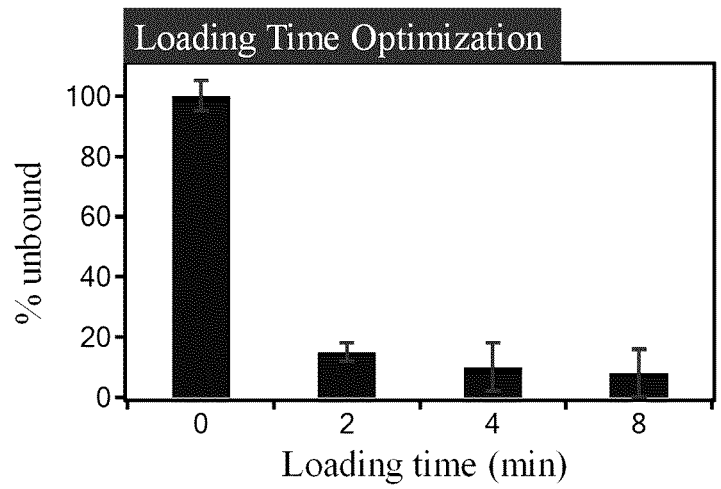
FIG. 7 graphically illustrates on-chip SPE parameter optimization, plotting loading time (a) and elution (b) optimization using fluorescein as a model system.
Figure 7:
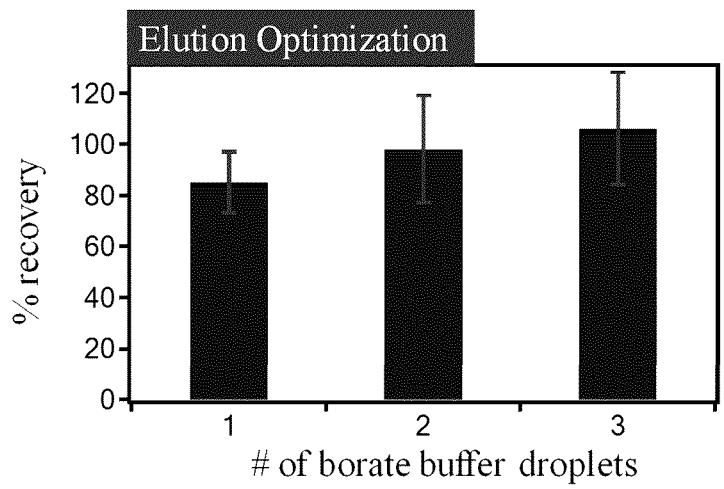

In both ZipTips® and microchannel based SPE devices, solutions containing a species to be extracted are actively passed through the stationary phase, ensuring efficient mass transfer of the species from solution into the hydrophobic stationary phase. In contrast, mass transfer of the species from a droplet into a PPM residing on a DMF array element is expected to be limited by slow diffusion. However, with fine tuning of the parameters, above 80% extraction efficiency was still obtainable as shown in FIG. 7(b) for C12 PPMs.

Although some examples provided in the present disclosure relate to the extraction of an analyte for subsequent analysis, it is to be understood that embodiments provided herein may be employed for a wide variety of applications, of which diagnostics is one non-limiting example.

The following examples are presented to enable those skilled in the art to understand and to practice embodiments of the present disclosure. They should not be considered as a limitation on the scope of the present embodiments, but merely as being illustrative and representative thereof.

EXAMPLES

Unless otherwise stated, all chemicals were obtained from Sigma-Aldrich (Oakville, ON) and used without further modification. All buffers were formed using deionized water that had a resistivity of 18 MΩ·cm at 25° C., filtered with nylon syringe filters from Millipore (Billerica, Mass., 0.2 μm pore diameter) and sonicated (5 min) prior to use. Ethanol (95%) and NaOH were purchased from ACP Chemicals (Montreal, QC). NaCl was purchased from Mallinckrodt Baker (Phillipsburg, N.J.). Fluorescein was purchased from Invitrogen (Burlington, ON). Cleanroom reagents and supplies included Parylene C dimer from Specialty Coating Systems (Indianapolis, Ind.), Teflon®-AF from DuPont (Wilmington, Del.), and Fluorinert™ FC-40 from Sigma (Oakville, ON). C18 Ziptips® were purchased from Millipore (Etobicoke, ON).

Example 1

DMF Device Fabrication with Integrated PPM for SPE

DMF devices were fabricated in the University of Toronto Emerging Communications Technology Institute (ECTI) cleanroom facility, using a transparent photomask printed at Pacific Arts and Design (Markham, ON). Glass devices bearing patterned chromium electrodes were formed by photolithography and etching as described previously,[23] and were coated with 7 μm of Parylene-C and 50 nm of Teflon®-AF. Parylene-C was applied using a vapor deposition instrument (Specialty Coating Systems), and Teflon®-AF was spin-coated (1% wt/wt in Fluorinert™ FC-40, 1000 rpm, 30 s) followed by post-baking on a hot-plate (160° C., 10 min). The polymer coatings were removed from contact pads by gentle scraping with a scalpel to facilitate electrical contact for droplet actuation. In addition to patterned devices, unpatterned indium tin oxide (ITO) coated glass substrates (Delta Technologies Ltd, Stillwater, Minn.) were coated with Teflon®-AF (50 nm, as above).

The device design, shown in FIG. 1, featured an array of eighty-eight actuation electrodes (2.2×2.2 mm ea.) connected to ten reservoir electrodes (5×5 mm ea.), with inter-electrode gaps of 40 μm. Devices were assembled with an unpatterned ITO-glass top plate and a patterned bottom plate separated by a spacer formed from three pieces of double-sided tape (total spacer thickness 270 μm). Unit droplets (covering a single driving electrode) were ~1 μL. To actuate droplets, driving potentials (220-300 $V_{pp}$) were generated by amplifying the output of a function generator (Agilent Technologies, Santa Clara, Calif.) operating at 18 kHz. As described elsewhere[20,23], droplets were sandwiched between the two plates and actuated by applying driving potentials between the top electrode (ground) and sequential electrodes on the bottom plate via the exposed contact pads. Droplet actuation was monitored and recorded by a CCD camera mounted on a lens.

Porous polymer monoliths (PPMs) were prepared via on-chip photopolymerization of a casting solution droplet manipulated by DMF. The C12 casting solution was prepared by mixing 279 μL of butyl acrylate, 150 μL of 1,3-butanediol diacrylate, 69 μL of lauryl acrylate, 2.5 mg of 2,2-dimethoxy-2-phenylacetophenone, and 1 mL of porogen including a 4:1:1 ratio of acetonitrile, 95% ethanol, and 5 mM phosphate buffer at pH 6.8. In similar way, C18 casting solution was prepared by mixing 2.5 mg of 2,2-dimethoxy-2-phenylacetophenone, 276 μL of butyl acrylate, 275 μL of octadecyl acrylate (0.3 g/mL in tetrahydrofuran), 150 μL of 1,3-butanediol diacrylate, and 796 μL of porogen including a 3:1:1 ratio of acetonitrile, 95% ethanol, and 5 mM phosphate buffer at pH 6.8. Wash buffer was formed from 0.5% (v/v) formic acid in deionized water and elution buffer was formed from 500 mM borate buffer at pH 9.0 (eluting fluorescein) or 0.1% (v/v) formic acid in acetonitrile (eluting peptides). A fluorescamine labelled peptide was used for direct comparison of extraction efficiency of C18 PPMs versus C18 ZipTips®. The labelling reaction was carried out as previously described (Udenfriend, S.; Stein, S.; Böhlen, P.; Dairman, W.; Leimgruber, W.; Weigele, M. "Fluorescamine: A Reagent for Assay of Amino Acids, Peptides, Proteins, and Primary Amines in the Picomole Range", Science 1972, 178, 871-872.). Briefly, a stock solution of labelled peptide was prepared by mixing 100 μL of fluorescamine (3 mg/mL in acetone), 10 μL of Angiotensin IV (10 mM in 10 mM borate buffer at pH 9), and 890 μL of acetone. The reaction mixture was allowed to incubate for at least 2 hours before being diluted 10× with 0.1% formic acid to form a sample solution for loading onto C18 PPMs.

Figure 5:
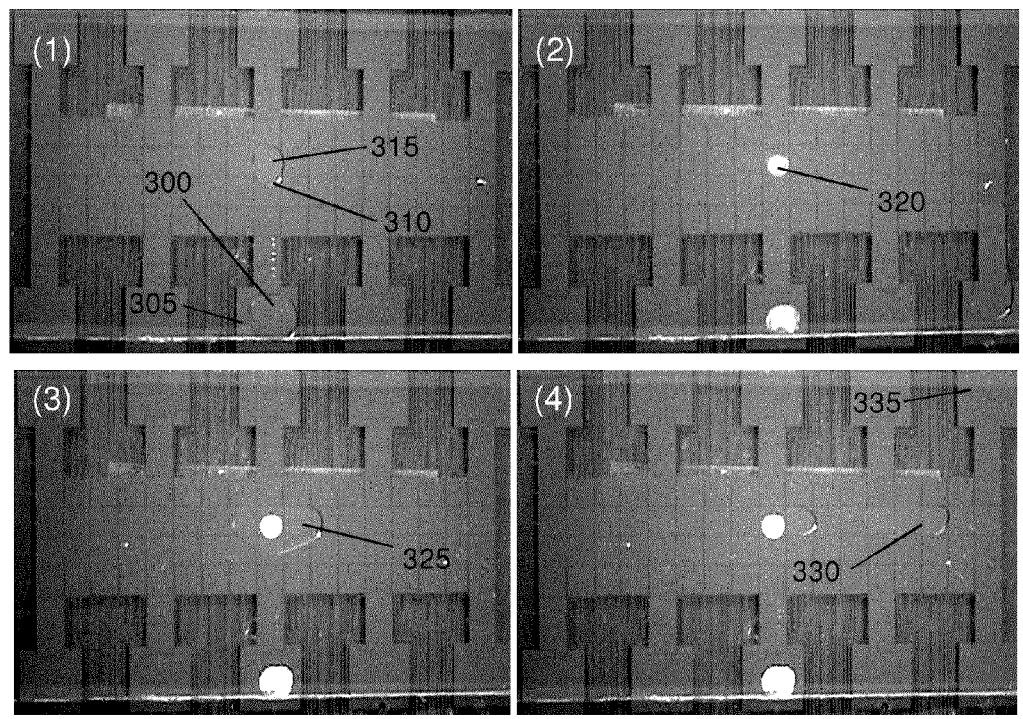
FIG. 5 shows frames from a movie illustrating the formation and activation of the C12 PPM on chip for SPE. In frame 1, 1 µL of C12 monomer solution was dispensed to the middle of the device. After UV exposure (100 W, 365 nm, 5 min), activation solvent (acetonitrile) was dispensed and actuated toward the C12 PPM (frame 2). The acetonitrile droplet was allowed to incubate on the C12 PPM (frame 3) for 2 minutes before being moved away to the waste/collector reservoir (frame 4). The steps are repeated for monolith activation, sample loading, washing, and elution.

All solutions were first pipetted onto the reservoir electrodes and then dispensed from them according to the indicated volume. As illustrated in FIG. 5, the PPM was formed by pipetting 5 μL casting solution 300 onto the middle reservoir electrode 305, then dispensing a 1 μL droplet 310 and translating it to a central electrode 315 (frame 1) where it was polymerized by exposure to UV radiation (100 W, 365 nm, 5 min). Next, the PPM was activated by dispensing and passing a 5 μL droplet of acetonitrile followed by a 5 μL droplet 325 of formic acid (0.5% v/v) over the monolith 320 (frame 2). After incubating for 2 minutes (frame 3), the activation solvent droplet 325 was moved away from the C12 PPM to the waste reservoir (frame 4). Once activated, one or more 1 μL sample droplets were dispensed and actuated to the PPM. After incubation, unbound sample was moved away and the PPM was washed with wash buffer (2×5 μL droplets), followed by elution of the bound sample with elution buffer (2×5 μL droplets).

Example 2

On-Chip PPM Characterization and Optimization

As described above, PPMs were first formed on chip by photopolymerizing casting solution droplets. FIG. 5 reveals the design of the device used for on chip photopolymerization (frame 1), followed by PPM activation (frame 2), sample loading (frame 3), rinsing (not shown), and elution (frame 4).

All characterization/optimization experiments were performed with at least three replicates on three separate PPMs/devices. To characterize the C12 PPM formed on-chip via DMF, scanning electron microscopy (SEM) was used to evaluate its porosity as compared to a PPM formed off-chip in a glass pipette. PPM specimens were imaged without coating using a TM-1000 SEM (Hitachi, Mississauga, ON).

Figure 6:
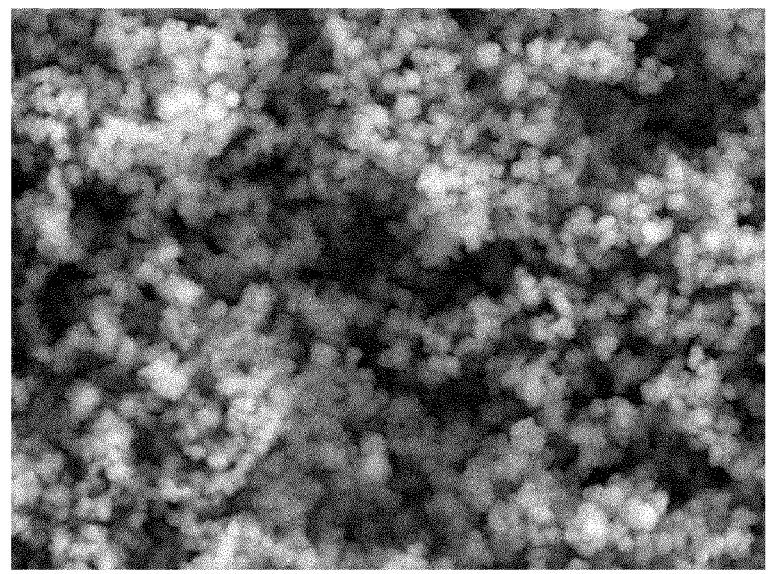
FIG. 6 is a SEM image of PPM formed on a DMF device.

The surface morphology of a C12 PPM formed on chip was compared with a C12 PPM formed in an enclosed glass pipette. Since C12 casting solution on a DMF chip is subject to an open environment during UV exposure, solvent evaporation, especially for 1 μL of monomer solution, would be a critical factor in determining the porosity of the formed PPM. Nonetheless, FIG. 6 shows that the porous morphology of PPMs formed on DMF devices strongly resembled PPMs formed in enclosed glass pipettes (SEM image not shown). This indicated that PPM morphology was unaffected by solvent evaporation.

In addition to porosity analysis, fluorescein was used as a model substrate to characterize the extraction efficiency of PPMs formed on DMF. For each of these experiments, fluorescein was loaded onto the activated PPM by driving a 1 μL sample droplet (5 μM fluorescein in 0.5% v/v aqueous formic acid) onto the PPM and allowing it to incubate for 2 min. After loading, the PPM was washed with aqueous formic acid droplets (0.5% v/v, 2×5 μL droplets) to remove unbound analyte. Then, fluorescein was eluted with 5 μL of borate buffer (500 mM, pH 9). The eluate was collected in a separate reservoir and was dried by heating on a hot plate (50° C., ~2 min). The dried sample was then resolubilized in 50 µL of borate buffer (500 mM, pH 9) and transferred to a 384-well plate for fluorescence measurement ($\lambda_{ex}$: 480 nm, $\lambda_{em}$: 520 nm) using a PHERAstar plate reader (BMG Labtech, Durham, N.C.).

In addition to porosity and extraction efficiency, sample loading time and elution steps were also characterized. For sample loading time optimization, 1 µL fluorescein droplets (5 µM in 0.5% v/v aqueous formic acid) were driven to PPMs and allowed to incubate for 2, 4, or 8 minutes. After incubation, sample droplets were moved away from the PPMs and dried. Their fluorescence intensities were measured as described above. For elution optimization, 1 µL fluorescein droplets (5 µM in 0.5% v/v aqueous formic acid) were loaded onto PPMs and were eluted in 1, 2, or 3 droplets of borate buffer (5 µL, 500 mM, pH 9). The droplets were dried and fluorescence was measured as described above.

As shown in FIG. 7(a), over 80% of sample was loaded onto the PPMs with an incubation time of 2 minutes. Although more (~10%) sample could be loaded onto the PPMs by increasing the incubation time from 2 minutes to 8 minutes, surface fouling would occur making droplet actuation difficult. Similarly, 2 elution droplets (shown in FIG. 7(b)) were enough to extract over 90% of bound sample off of the PPMs.

Using the above optimized parameters, the performance of C18 PPMs was compared with commercially available C18 ZipTips®. C18 PPMs were prepared as described above. After UV exposure, C18 PPMs were activated the same way as C12 PPMs described above. Following activation, 1 µL of labelled peptide sample (10 µM in 0.1% formic acid) was loaded onto a C18 PPM by actuating the droplet over the polymerized monolith. Next, the peptide sample was allowed to incubate on the PPM for 2 minutes before the PPM was washed as described above. Finally, the bound sample was eluted by passing the elution buffer (2×5 µL droplets of 0.1% formic acid in acetonitrile) over the PPM. The fluorescence of extracted peptide samples was measured using the plate reader ($\lambda_{ex}$: 390 nm, $\lambda_{em}$: 460 nm) as described above. For the extraction of labelled peptides using C18 Ziptips®, activation, washing and elution steps were carried out as per the manufacturer's instructions without modification. The detected fluorescence intensities were compared with the control sample (1 µL fluorescamine labelled peptide) which had been subject neither to extraction via C18 PPMs on chip nor to extraction via ZipTips®. As shown below in Table 1, the extraction efficiency of C18 PPMs was very comparable to the C18 ZipTips®.

TABLE 1

|  | Extraction Efficiency |
|---|---|
| C18 Ziptip ® | 92% ± 14% |
| C18 PPM | 56% ± 2% |

Example 3

On-Chip SPE for Preparative Preconcentration

An on-chip preconcentration of fluorescein was performed using a device design as illustrated in FIG. 4. The new design featured 12 large electrodes (7.5 mm×7.5 mm) for moving sample and solvent droplets (unit volume of 12 µL), and 19 small electrodes (2.2 mm×2.2 mm) for moving monolith casting solution and elution buffer droplets (unit volume of 1 µL).

To achieve preconcentration, first, 12 µL of fluorescein (5 µM in 0.5% v/v aqueous formic acid) was loaded onto an activated C12 PPM (bed volume ~1 µL). The sample was allowed to incubate on the PPM for ~8 minutes while constantly actuating the sample droplet back and forth along the 4 adjacent large electrodes (2 on each side). The remaining sample was actuated away from the monolith and back to the sample reservoir electrode. Next, 12 µL of wash buffer (0.5% formic acid) was actuated to the monolith to remove any unbound sample.

After washing, the bound sample was eluted by bringing 1 µL of elution buffer (500 mM borate buffer at pH 9) to the PPM. After 2 minutes of incubation, the device was disassembled and the extracted sample was pipetted off the device and diluted in 49 µL of borate buffer (500 mM, pH 9). The fluorescence intensity was measured and compared with the control sample, consisting of 1 µL of fluorescein (5 µM in 0.5% v/v aqueous formic acid) diluted with 49 µL of borate buffer.

Figure 8:
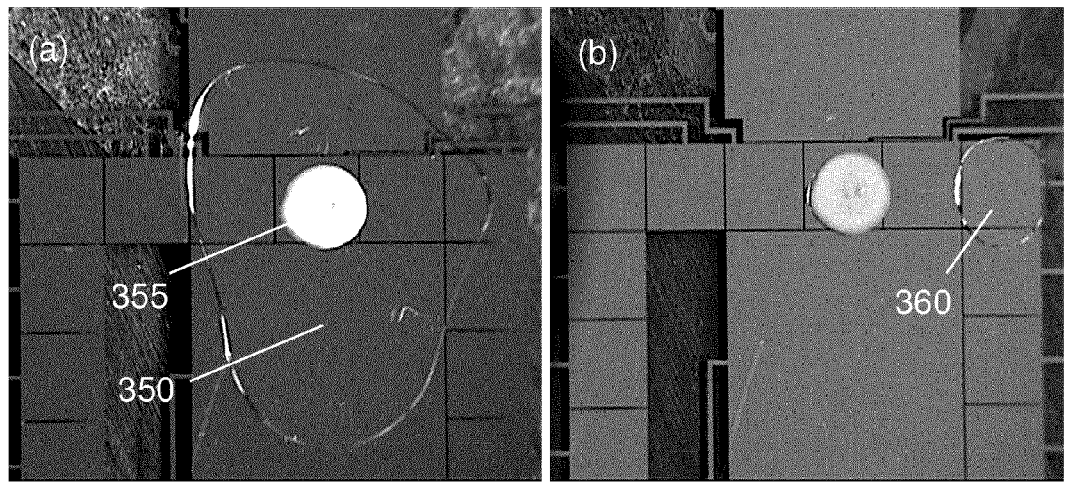
FIG. 8 provides images demonstrating the process of preconcentating the sample on-chip using C12 porous polymer monoliths. In image (a), a 12 µL sample droplet was actuated towards the activated PPM. In image (b), the PPM was washed and a 1 µL droplet of elution buffer was actuated to extract the sample off of the PPM.
Figure 9:
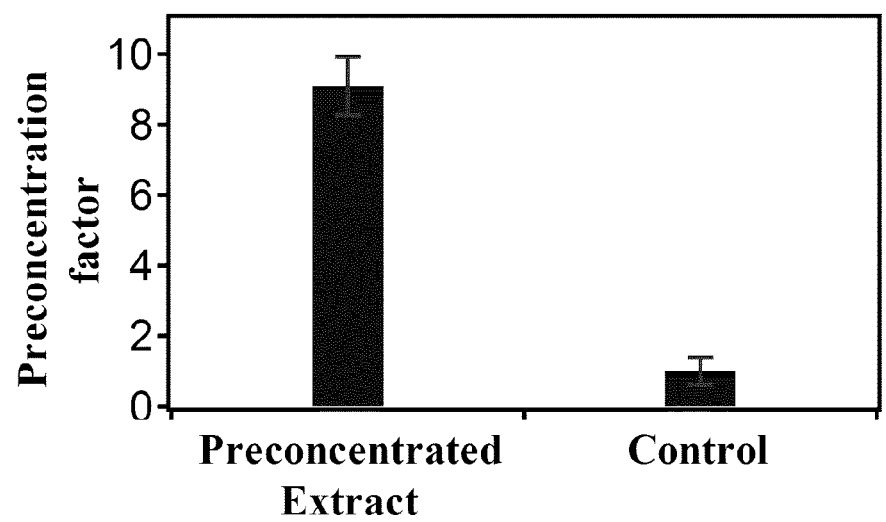
FIG. 9 is a bar graph plotting a preconcentration factor of 9.0 in the extracted sample versus the control (1 µL fluorescein sample).

A series of images demonstrating the preconcentration process using C12 porous polymer monoliths are shown in FIG. 8. In image (a), a 12 µL sample droplet 350 was actuated towards the activated PPM 355. In image (b), the PPM was washed and a 1 µL droplet 360 of elution buffer was actuated to extract the sample off of the PPM. Using the design shown in FIG. 4 and fluorescein as a model substrate, a preconcentration factor of 10.4 was demonstrated, as shown in FIG. 9.

Example 5

On-Chip SPE for Preparative Desalting

An on-chip desalting of angiotensin II (AngII, 1 µM, MW 1046 Da) in a solution containing sodium chloride (100 mM) was performed prior to nano-electrospray mass spectrometric (nanoESI-MS) analysis. First, a 1 µL droplet of sample solution was dispensed onto the PPM and incubated (2 min). After loading, the PPM was rinsed with deionized water (2×5 µL droplets), and a droplet of formic acid (0.1%, v/v) in acetonitrile (5 µL) was used to elute the sample, which was collected in a separate reservoir and allowed to evaporate at room temperature. The eluate was resolubilized in 50 µL of 50% acetonitrile containing 0.1% formic acid, and analysed via nanoESI-MS (LTQ Finnigan, Thermo Electron Corp., FL). As a control, the same sample (without desalting) was analyzed by nanoESI-MS for comparison. The applied spray voltage varied between 1.7-2.0 kV and the flow rate of the syringe pump and capillary temperature were kept constant at 0.5 µL/min and 200° C., respectively. Each experiment and control was performed in triplicate.

Figure 10:
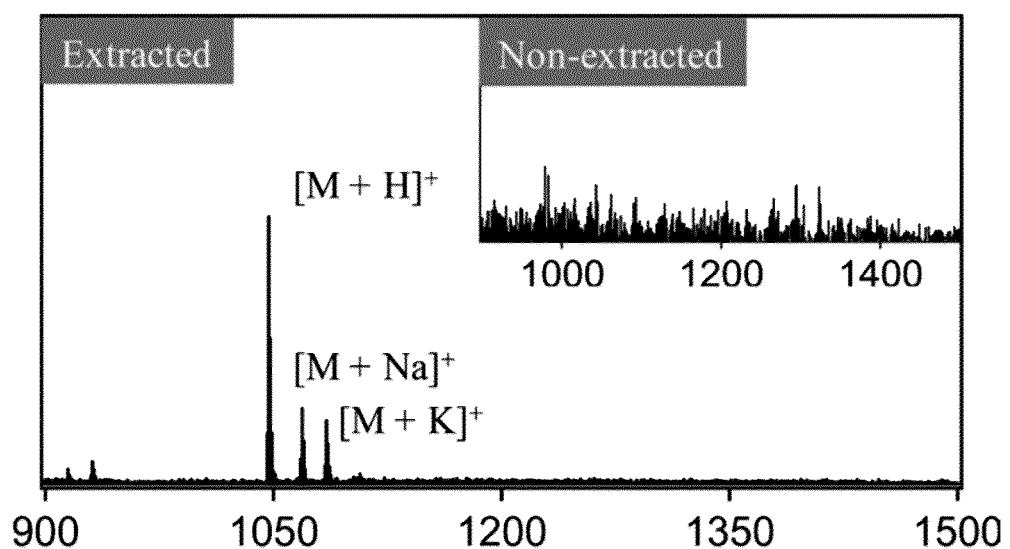
FIG. 10 plots nanoESI mass spectra of non-desalted (inset) and desalted angiotensin II.

As shown in FIG. 10 (inset), non-desalted (i.e. non-extracted) sample yielded no peaks at m/z=1047 due to ion suppression by the salt matrix. However, after desalting (i.e. extraction) (FIG. 10), nanoESI-MS analysis displayed a strong signal at m/z=1047 representing the singly protonated Angiotensin II ion.

Example 6

On-Chip SPE Using One-Plate DMF Techniques

To prevent evaporation and to generate a disk-shaped PPM, the PPM was formed using two-plate DMF geometry.

First, a 10-µL droplet of C12 casting solution (described above) was pipetted onto an electrode of a one-plate DMF device. Then, the monomer droplet was sandwiched by using another Teflon® AF-coated glass slide elevated with 270-µm spacers (double sided tape, as described above). Next, monomer droplet was exposed to UV radiation (100 W, 365 nm, 5 min). After exposure, the top slide and spacers were removed, leaving a PPM disk on the one plate DMF device.

Figure 11:
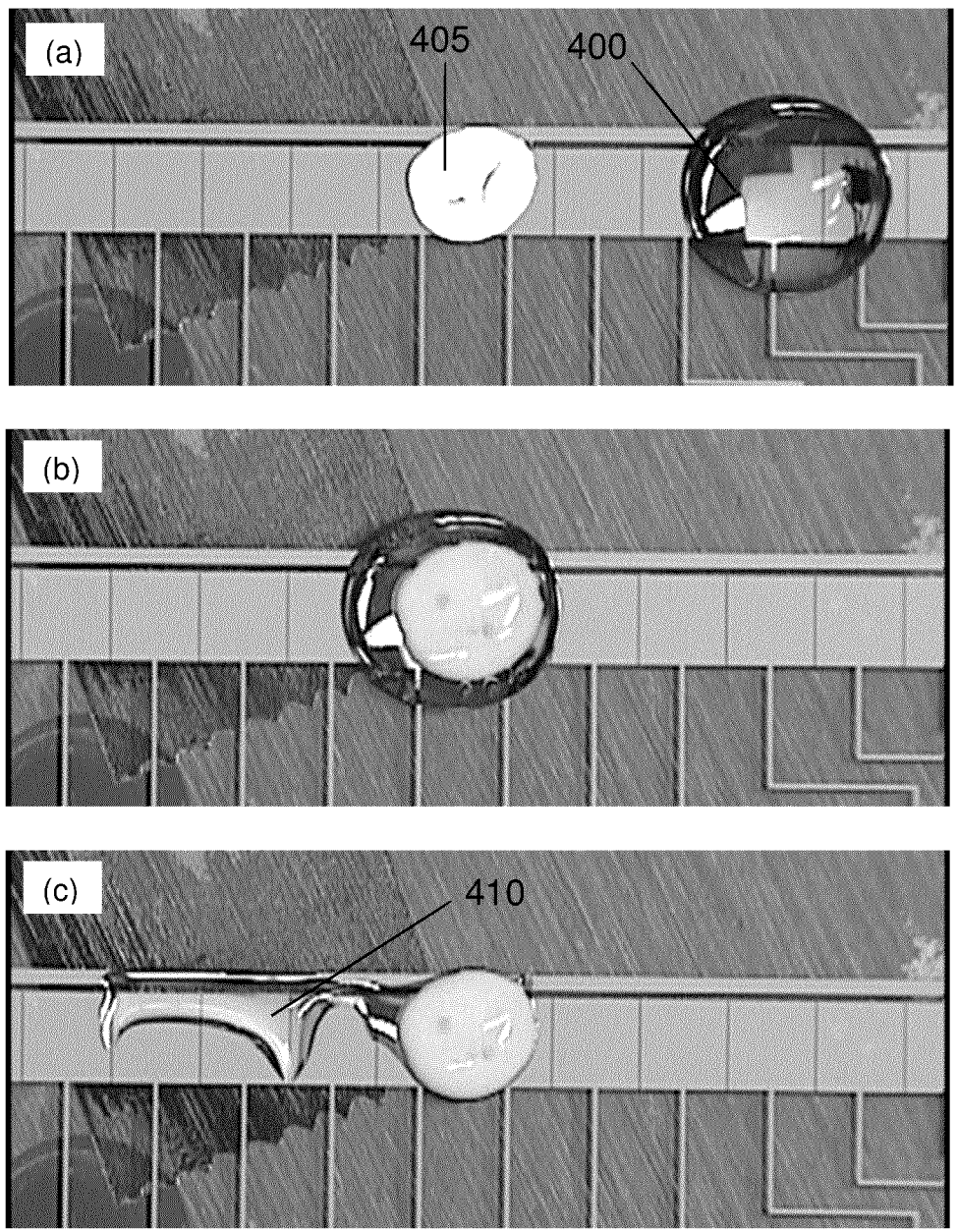
FIG. 11 shows frames from a movie illustrating the actuation of an acetonitrile droplet onto and off of a PPM on a one-plate DMF device. In frame (a), 50 µL of acetonitrile is actuated towards the C12 PPM where it is allowed to incubate on the PPM (frame (b)). In frame (c), the acetonitrile droplet is extracted from the PPM.

As shown in FIG. 11(a), a droplet of acetonitrile (50 µL) was pipetted onto the device. The droplet was actuated onto the PPM 405 by applying potentials (720 $V_{pp}$, 18 kHz) to consecutive actuation electrodes, as shown in FIG. 11(b). The acetonitrile 410 was then actuated off of the PPM in the same manner, as shown in FIG. 11(c).

Example 7

Preparation of Porous Monolith with Integrated Beads

Beads were trapped in C4 monoliths as described below. A C4 casting solution was prepared by mixing 348 µL of butyl acrylate, 150 µL of 1,3-butanediol diacrylate, 2.5 mg of 2,2-dimethoxy-2-phenylacetophenone, and 1 mL of porogen including a 4:1:1 ratio of acetonitrile, 95% ethanol, and 5 mM phosphate buffer at pH 6.8.

C18-functionalized polystyrene beads with 5 µm diameters (1 mg/mL) were suspended in the prepared C4 casting solution. The PPM was formed via photopolymerization by exposing to UV light (100 W, 365 nm, 5 min).

It is expected that beads may also be cast in a C1 monolith. A C1 casting solution may be prepared by mixing 348 µL of methyl acrylate, 150 µL of 1,3-butanediol diacrylate, 2.5 mg of 2,2-dimethoxy-2-phenylacetophenone, and 1 mL of porogen including a 3:1:1 ratio of acetonitrile, 95% ethanol, and 5 mM phosphate buffer at pH 6.8.

Example 8

On-Chip SPE for Preparative Surfactant Removal

In the present example, an on-chip removal of surfactant from a sample of angiotensin II (AngII, 1 µM, MW 1046 Da) in a solution containing Pluronic F68 (0.05% w/v) was performed prior to nano-electrospray mass spectrometric (nanoESI-MS) analysis.

First, a 1 µL droplet of sample solution was dispensed onto the PPM and incubated (2 min). After loading, the PPM was rinsed with deionized water (2×5 µL droplets), and a droplet of formic acid (0.1%, v/v) in acetonitrile (5 µL) was used to elute the sample, which was collected in a separate reservoir and allowed to evaporate at room temperature. The eluate was resolubilized in 50 µL of 50% acetonitrile containing 0.1% formic acid, and analyzed via nanoESI-MS (LTQ Finnigan, Thermo Electron Corp., FL). As a control, the same sample (without removal of surfactant) was analyzed by nanoESI-MS for comparison. The applied spray voltage varied between 1.7-2.0 kV and the flow rate of the syringe pump and capillary temperature were kept constant at 0.5 µL/min and 200° C., respectively. Each experiment and control was performed in triplicate.

Figure 12:
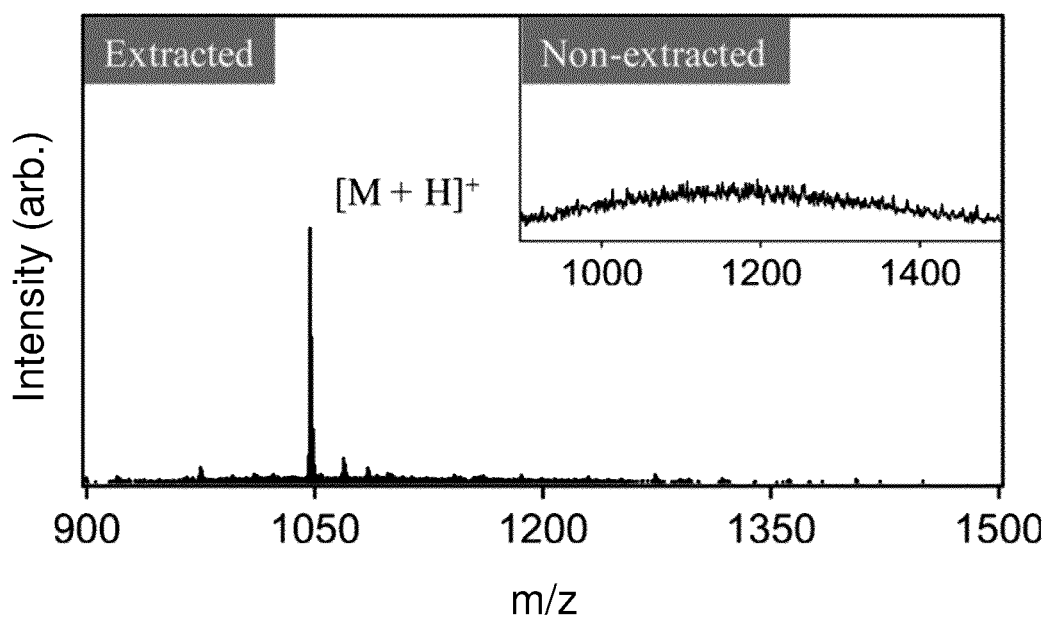
FIG. 12 plots nanoESI mass spectra of angiotensin II without removal of surfactant (inset) and with removal of surfactant.

As shown in FIG. 12 (inset), non-extracted surfactant-containing sample yielded no peaks at m/z=1047 due to ion suppression by the surfactant matrix. However, after surfactant removal (FIG. 12), nanoESI-MS analysis displayed a strong signal at m/z=1047 representing the singly protonated Angiotensin II ion.

Example 9

Evaluation of Extraction Efficiency Using C12 PPMs

In the present example, a fluorescamine labeled peptide was used for direct comparison of extraction efficiency of C12 PPMs versus C18 ZipTips®. The labeling reaction was carried out as described above in Example 2. Briefly, a stock solution of labeled peptide was prepared by mixing 100 µL of fluorescamine (3 mg/mL in acetone), 10 µL of Angiotensin IV (10 mM in 10 mM borate buffer at pH 9), and 890 µL of acetone. The reaction mixture was allowed to incubate for at least 2 hours before being diluted 10× with 0.1% formic acid to form a sample solution. C12 PPMs were prepared and activated as described above in Example 1. Following activation, 1 µL of labeled peptide sample (10 µM in 0.1% formic acid) was loaded onto a C12 PPM by actuating the droplet over the polymerized monolith. Next, the peptide sample was allowed to incubate on the PPM for 2 minutes before the PPM was washed as described above. Finally, the bound sample was eluted by passing the elution buffer (2×5 µL droplets of 0.1% formic acid in acetonitrile) over the PPM. The fluorescence of extracted peptide samples was measured using the plate reader ($\lambda_{ex}$: 390 nm, $\lambda_{em}$: 460 nm) as described above. For the extraction of labeled peptides using C18 ZipTips®, activation, washing and elution steps were carried out as per the manufacturer's instructions without modification. The detected fluorescence intensities were compared with the control sample (1 µL fluorescamine labeled peptide) which had been subject neither to extraction via C12 PPMs on chip nor to extraction via ZipTips®. As shown in Table 2, the extraction efficiency of C12 PPMs was very comparable to the C18 ZipTips®.

TABLE 2

| | Extraction Efficiency |
|---|---|
| C18 Ziptip ® | 92% ± 5% |
| C12 PPM | 93% ± 14% |

Example 10

Solid-Phase Extractions using Monoliths with Strong Cation Exchange Functionality Casting solution for the formation of strong cation exchange (SCX) monoliths was formed by dissolving glycidyl methacrylate (900 µL), ethylene glycol dimethacrylate (300 µL) and 2,2-dimethoxy-2-phenylacetophenone (12 mg) in a porogenic solvent consisting of 1-propanol (1.05 mL), 1,4-butanediol (600 µL) and water (150 µL). PPMs were formed by pipetting a 2 µL droplet of casting solution between two Teflon AF-coated glass slides, spaced 450 µm apart using double-sided tape, followed by UV irradiation (5 min, 365 nm, 100 W). The resulting PPMs were rinsed with methanol and allowed to react with an aqueous solution of sodium sulphite (1 M, 24 h), followed by reaction with a nitric acid solution (10 mM, 10 min). Finally, PPMs were rinsed with deionised water and sandwiched between the bottom substrate and the top ITO slide of a DMF device, spaced apart with 270 μm of double-sided tape.

Extraction efficiency using SCX PPMs on DMF were characterized using the peptide angiotensin IV (Ang IV) as a model analyte. The following steps were carried out by actuating solution droplets on the DMF device. First, the PPM was equilibrated with a 5 μL droplet of sodium citrate buffer (10 mM, pH 3, 2 min). Next 1 μL of an Ang IV sample solution (150 μM) in sodium citrate buffer (10 mM, pH 3) was loaded onto the PPM and allowed to incubate for 2 minutes. After removal of the sample droplet, the PPM was rinsed with a 5 μL droplet of sodium citrate buffer (10 mM, pH 3).

The Ang IV bound to the PPM was then eluted using two 5 μL droplets of aqueous sodium chloride solution (1 M) buffered with sodium citrate (10 mM, pH3). The eluate was collected and labeled off-chip with fluorescamine. The labeling reaction was carried out by adding sodium bicarbonate (1 μL, 100 mM, pH 9), acetonitrile (43.8 μL) and fluorescamine (0.25 μL, 1 mg/mL in acetonitrile) to the eluate. The labeled Ang IV in the eluate was then immediately quantified by fluorescence measurement ($\lambda_{ex}$: 390 nm, $\lambda_{em}$: 460 nm) using a PHERAstar plate reader (BMG Labtech, Durham, N.C.). Using the above method for SCX extractions on DMF, an extraction efficiency of 74% was achieved.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES (1) Kutter, J. P.; Jacobson, S. C.; Matsubara, N.; Ramsey, J. M. "Solvent-Programmed Microchip Open-Channel Electrochromatography", *Analytical Chemistry* 1998, 70, 3291-3297.

(2) Kutter, J. P.; Jacobson, S. C.; Ramsey, J. M. "Solid phase extraction on microfluidic devices", *Journal of Microcolumn Separations* 2000, 12, 93-97.

(3) Bergkvist, J.; Ekstrom, S.; Wallman, L.; Lofgren, M.; Marko-Varga, G.;
Nilsson, J.; Laurell, T. "Improved chip design for integrated solid-phase microextraction in on-line proteomic sample preparation", *Proteomics* 2002, 2, 422-429.

(4) Ekstrom, S.; Malmstrom, J.; Wallman, L.; Lofgren, M.; Nilsson, J.; Laurell, T.; Marko-Varga, G. "On-chip microextraction for proteomic sample preparation of in-gel digests", *Proteomics* 2002, 2, 413-421.

(5) Ekstrom, S.; Wallman, L.; Hok, D.; Marko-Varga, G.; Laurell, T. "Miniaturized solid-phase extraction and sample preparation for MALDI MS using a microfabricated integrated selective enrichment target", *Journal of Proteome Research* 2006, 5, 1071-1081.

(6) Ekstrom, S.; Wallman, L.; Helldin, G.; Nilsson, J.; Marko-Varga, G.; Laurell, T. "Polymeric integrated selective enrichment target (ISET) for solid-phase-based sample preparation in MALDI-TOF MS", *Journal of Mass Spectrometry* 2007, 42, 1445-1452.

(7) Jemere, A. B.; Oleschuk, R. D.; Ouchen, F.; Fajuyigbe, F.; Harrison, D. J. "An integrated solid-phase extraction system for sub-picomolar detection", *Electrophoresis* 2002, 23, 3537-3544.

(8) Li, J.; LeRiche, T.; Tremblay, T. L.; Wang, C.; Bonneil, E.; Harrison, D. J.; Thibault, P. "Application of microfluidic devices to proteomics research: identification of trace-level protein digests and affinity capture of target peptides", *Molecular & cellular proteomics: MCP* 2002, 1, 157-168.

(9) Oleschuk, R. D.; Shultz-Lockyear, L. L.; Ning, Y.; Harrison, D. J. "Trapping of bead-based reagents within microfluidic systems: On-chip solid-phase extraction and electrochromatography", *Analytical Chemistry* 2000, 72, 585-590.

(10) Lettieri, G. L.; Dodge, A.; Boer, G.; De Rooij, N. F.; Verpoorte, E. "A novel microfluidic concept for bioanalysis using freely moving beads trapped in recirculating flows", *Lab on a Chip-Miniaturisation for Chemistry and Biology* 2003, 3, 34-39.

(11) Foote, R. S.; Khandurina, J.; Jacobson, S. C.; Ramsey, J. M. "Preconcentration of proteins on microfluidic devices using porous silica membranes", *Analytical Chemistry* 2005, 77, 57-63.

(12) Hatch, A. V.; Herr, A. E.; Throckmorton, D. J.; Brennan, J. S.; Singh, A. K. "Integrated preconcentration SDS-PAGE of proteins in microchips using photopatterned cross-linked polyacrylamide gels", *Analytical Chemistry* 2006, 78, 4976-4984.

(13) Petersen, N. J.; Jensen, H.; Hansen, S. H.; Foss, S. T.; Snakenborg, D.; Pedersen-Bjergaard, S. "On-chip electro membrane extraction", *Microfluidics and Nanofluidics* 2010, 1-8.

(14) Bonneil, E.; Li, J.; Tremblay, T. L.; Bergeron, J. J.; Thibault, P. "Integration of solid-phase extraction membranes for sample multiplexing: Application to rapid protein identification from gel-isolated protein extracts", *Electrophoresis* 2002, 23, 3589-3598.

(15) Yu, C.; Davey, M. H.; Svec, F.; Frechet, J. M. J. "Monolithic porous polymer for on-chip solid-phase extraction and preconcentration prepared by photoinitiated in situ polymerization within a microfluidic device", *Analytical Chemistry* 2001, 73, 5088-5096.

(16) Yu, C.; Xu, M.; Svec, F.; Frechet, J. M. J. "Preparation of monolithic polymers with controlled porous properties for microfluidic chip applications using photoinitiated free-radical polymerization", *Journal of Polymer Science, Part A: Polymer Chemistry* 2002, 40, 755-769.

(17) Lee, J.; Moon, H.; Fowler, J.; Schoellhammer, T.; Kim, C. J. "Electrowetting and electrowetting-on-dielectric for microscale liquid handling", *Sensors and Actuators, A: Physical* 2002, 95, 259-268.

(18) Pollack, M. G.; Fair, R. B.; Shenderov, A. D. "Electrowetting-based actuation of liquid droplets for microfluidic applications", *Applied Physics Letters* 2000, 77, 1725-1726.

(19) Wheeler, A. R. "Chemistry: Putting electrowetting to work", *Science* 2008, 322, 539-540.

(20) Abdelgawad, M.; Freire, S. L. S.; Yang, H.; Wheeler, A. R. "All-terrain droplet actuation", *Lab on a Chip-Miniaturisation for Chemistry and Biology* 2008, 8, 672-677.

(21) Jebrail, M. J.; Wheeler, A. R. "Digital microfluidic method for protein extraction by precipitation", *Analytical Chemistry* 2009, 81, 330-335.

(22) Mousa, N. A. J., M. J.; Yang, H.; Abdelgawad, M.; Metalnikov, P.; Chen, J.; Wheeler, A. R.; Casper, R. F. "Droplet-Scale Estrogen Assays in Breast Tissue, Blood, and Serum", *Sci. Trans. Med.* 2009, 1, 1 ra2.

(23) Jebrail, M. J.; Luk, V. N.; Shih, S. C. C.; Fobel, R.; Ng, A. H. C.; Yang, H.; Freire, S. L. S.; Wheeler, A. R. *Journal of Visualized Experiments.* 2009, 33, DOI: 10.3791/1603.

Therefore what is claimed is:

1. A digital microfluidic device comprising:
    a substrate;
    an array of electrically addressable digital microfluidic elements provided on said substrate; and
    a solid phase extraction material contacting an element of said array, in absence of a supporting microfluidic channel, said solid phase extraction material being configured for the extraction of a species from solution, and for the subsequent elution of the extracted species from the solid phase extraction material upon contact with a suitable elution buffer;
    wherein said solid phase extraction material is positioned such that a liquid droplet is contacted with said solid phase extraction material when said liquid droplet transported to said element.

2. The device according to claim 1 wherein a size of said solid phase extraction material is selected such that a droplet may be transported to and from said element under electrical actuation of said array.

3. The device according to claim 1 wherein said solid phase extraction material is porous.

4. The device according to claim 1 wherein said solid phase extraction material is selected from the group consisting of porous polymer monoliths and hydrogels.

5. The device according to claim 1 wherein said solid phase extraction material has a cross-sectional area less than an area of said element.

6. The device according to claim 5 wherein said solid phase extraction material is located at a central portion of said element.

7. The device according to claim 1 wherein said elements are formed on said substrate, and wherein each element of said array includes an electrode coated with an electrical insulating layer having a hydrophobic surface.

8. The device according to claim 7 wherein said substrate and said array define a one-plate digital microfluidic array.

9. The device according to claim 7 wherein said substrate and said array of electrically addressable digital microfluidic elements define a first plate of a two-plate digital microfluidic array, said device further including a second plate including an electrode coated with a layer having a hydrophobic surface, and a spacer for defining a gap between said first plate and said second plate.

10. The device according to claim 9 wherein said solid phase extraction material is provided between said first plate and said second plate.

11. The device according to claim 10 wherein said solid phase extraction material is clamped between said first plate and said second plate.

12. The device according to claim 10 wherein a shape of said solid phase extraction material is substantially cylindrical.

13. The device according to claim 1 wherein said array of electrically addressable digital microfluidic elements is a first array of electrically addressable digital microfluidic elements, said first array including said element, and said device further comprising a second array of electrically addressable digital microfluidic elements provided on said substrate, wherein elements of said second array are larger than elements of said first array, and wherein said second array of electrically addressable digital microfluidic elements intersects said first array of electrically addressable digital microfluidic elements at said element.

14. The device according to claim 1 wherein said solid phase extraction material is functionalized.

15. The device according to claim 1 further comprising one or more reservoirs, wherein said one or more reservoirs are in dropwise flow communication with said array of elements under electrical actuation of said array.

16. The device according to claim 1 further comprising a support for positioning said solid phase extraction material relative to said element.

17. The device according to claim 1 wherein said solid phase extraction material is selected from the group consisting of strong cation exchange PPMs, strong anion exchange PPMs, weak cation exchange PPMs, weak anion exchange PPMs, normal phase PPMs, acrylamide gels, agarose gels, hydrogels, chiral PPMs, trapped glass beads, trapped polymeric beads, and affinity phases where a small molecule has an affinity for a large molecule.

18. A method for performing solid phase extraction of a species from a sample, the method comprising the steps of:
    providing a digital microfluidic device including a substrate, an array of electrically addressable digital microfluidic elements provided on the substrate, and a solid phase extraction material contacting an element of the array;
    providing a liquid sample at a location addressable by the array;
    actuating the array to transport a sample droplet to contact the element such that the sample droplet contacts the solid phase extraction material;
    incubating the sample droplet while maintaining contact of the sample droplet with the solid phase extraction material;
    transporting the sample droplet to another location addressable by the array;
    providing a wash buffer at a location addressable by the array;
    actuating the device to transport a wash buffer droplet to contact the element such that the wash buffer droplet contacts the solid phase extraction material;
    transporting the wash buffer droplet to another location addressable by the array;
    providing an elution buffer at a location addressable by the array, wherein elution buffer is suitable for eluting the species from the solid phase extraction material;
    actuating the array to transport an elution buffer droplet to the element; and
    incubating the elution buffer droplet while maintaining contact of the elution buffer droplet with the solid phase extraction material for a time suitable for elution of the species from the solid phase extraction material to the elution buffer droplet.

19. The method according to claim 18 further comprising the step of actuating the array to transport the elution buffer droplet to another element of the array.

20. The method according to claim 18 wherein the volume of the elution buffer droplet is less than the volume of the sample droplet for concentrating the species.

21. The method according to claim 18 further comprising the step of activating the solid phase extraction material prior to the step of actuating the device to transport the sample droplet to contact the element.

22. The method according to claim 21 wherein the step of activating the solid phase extraction material includes the steps of:
    providing an activation buffer at a location addressable by the array, wherein activation buffer is suitable for activating the solid phase extraction material;

actuating the array to transport an activation buffer droplet to contact the element such that the activation buffer contacts the solid phase extraction material;

incubating the activation buffer droplet while maintaining contact of the activation buffer droplet with the solid phase extraction material; and transporting the activation buffer droplet to another location addressable by the array.

23. The method according to claim 18 wherein the step of incubating the sample droplet further comprises actuating the device to achieve motion of the sample droplet relative to the solid phase extraction material.

24. The method according to claim 18 wherein the step of incubating the elution buffer droplet further comprises actuating the device to achieve motion of the elution buffer droplet relative to the solid phase extraction material.

25. The method according to claim 18 wherein the step of actuating the device to transport a wash buffer droplet to contact the element such that the wash buffer droplet contacts the solid phase extraction material further comprises actuating the device to achieve motion of the wash buffer droplet relative to the solid phase extraction material when contacting the solid phase extraction material.

26. The method according to claim 18 wherein:

the array of electrically addressable digital microfluidic elements includes a first array of electrically addressable digital microfluidic elements and a second array of electrically addressable digital microfluidic elements provided on a common substrate, the first array including the element, wherein elements of the second array are larger than elements of the first array, and wherein the second array of electrically addressable digital microfluidic elements intersects the first array of electrically addressable digital microfluidic elements at the element;

wherein the step of actuating the array to transport a sample droplet to contact the element includes transporting the sample droplet among elements of the second array; and wherein the step of actuating the array to transport the elution buffer droplet to the element includes transporting the elution buffer droplet among elements of the first array.

27. The method according to claim 26 wherein a concentration of the species is determined by selecting a suitable relative size of the first array elements and second array elements.

* * * * *